United States Patent
Quay et al.

(10) Patent No.: US 6,287,521 B1
(45) Date of Patent: *Sep. 11, 2001

(54) METHODS AND DEVICES FOR OBTAINING AND ASSAYING MAMMARY FLUID SAMPLES FOR EVALUATING BREAST DISEASES, INCLUDING CANCER

(75) Inventors: Steven C. Quay; Debra L. Quay, both of Edmonds, WA (US)

(73) Assignee: Atossa Healthcare, Inc., Edmonds, WA (US)

( * ) Notice: Subject to any disclaimer, the term of this patent is extended or adjusted under 35 U.S.C. 154(b) by 0 days.
This patent is subject to a terminal disclaimer.

(21) Appl. No.: 09/027,362

(22) Filed: Feb. 20, 1998

Related U.S. Application Data

(63) Continuation-in-part of application No. 08/709,207, filed on Aug. 27, 1996, now Pat. No. 5,798,266.

(51) Int. Cl.[7] .......................... G01N 33/48; G01N 33/53; A61N 1/06; A61N 1/00
(52) U.S. Cl. ................... 422/101; 435/6; 435/7; 435/7.1; 435/7.2; 435/7.21; 435/24; 435/30; 435/296; 435/723; 435/810; 435/975; 436/64; 436/501; 436/523; 436/531; 436/161; 436/162; 436/177; 436/178; 436/807; 436/808; 436/810; 436/813; 436/574; 436/576; 436/507; 436/508; 436/514; 604/74; 604/75; 604/76; 604/315; 604/319; 604/320; 604/346
(58) Field of Search .......................... 435/6, 7, 7.1, 7.2, 435/7.21, 723, 29, 30, 296, 810, 975; 422/101, 104, 100; 436/501, 523–531, 64, 161, 162, 177, 178, 807, 808, 810, 813, 574, 576; 604/74–76, 315

(56) References Cited

U.S. PATENT DOCUMENTS

| | | | |
|---|---|---|---|
| 3,786,801 | 1/1974 | Sartorius | 128/2 F |
| 4,147,514 | 4/1979 | Magers et al. | 23/230 B |
| 4,759,747 | * 7/1988 | Aida et al. | 604/74 |
| 4,857,051 | * 8/1989 | Larsson | 604/74 |
| 4,929,229 | 5/1990 | Larsson | 604/74 |
| 5,007,899 | 4/1991 | Larsson | 604/74 |
| 5,295,957 | * 3/1994 | Aida et al. | 604/74 |
| 5,601,531 | 2/1997 | Silver | 604/74 |
| 5,798,266 | * 8/1998 | Quay et al. | 436/64 |

OTHER PUBLICATIONS

93:215481p, 1980, Russia–USSR, Izv. Akad. Nauk Kaz. Senological Biology 1980, vol. 4, pp. 64–66.
Amico et al., "A Novel Oxytocin–Like and Vasotocin–Like Peptide in Human Plasma after Administration of Estrogen," *J. Clin. Endorinology and Metabolism 60* (1): 5–12, 1985.

(List continued on next page.)

*Primary Examiner*—Long V. Le
*Assistant Examiner*—Lisa V. Cook
(74) *Attorney, Agent, or Firm*—Townsend and Townsend and Crew LLP

(57) ABSTRACT

Non-invasive methods are provided for obtaining biological samples of mammary fluid or mammary fluid components by administering oxytocin to a patient to stimulate expression of mammary fluid. During or after mammary fluid expression, a biological sample is collected in the form of whole mammary fluid, whole cells or cellular components, other selected liquid or solid fractions of the mammary fluid, purified or bulk proteins, glycoproteins, peptides, nucleotides or other desired Constituents of mammary fluid. Methods and kits are also provided for determining the presence or amount of a breast disease marker in biological samples of mammary fluid or mammary fluid components obtained according to the above sample collection methods. Also provided within the invention are novel breast pump and breast pump adapter devices which incorporate a solid phase sample collection medium integrated within the breast pump or adapter or otherwise fluidly connected therewith. These devices collect a sample of expressed breast fluid by contacting the fluid with a solid phase sample collection medium while the pump or adapter is applied to the breast.

18 Claims, 5 Drawing Sheets

OTHER PUBLICATIONS

Ceriani et al., "Diagnostic ability of different human milk fat globule antigens in breast cancer," *Breast Cancer Research and Treatment* 15:161–174, 1990.

Cobo, "Characteristics of the spontaneous mile ejecting activity occurring during human lactation," *J. Perinat. Med.* 21:77–85, 1993.

Domagala et al., "Nuclear p53 Protein Accumulates Preferentially in Medullary and High–Grade Ductal but Rarely in Lobular breast Carcinomas," *Am. J. Pathology* 142(3):669–674, 1993.

Eskelinen et al., "Efficient Test for Cancer Antigens: Decreased Levels of Cancer Antigen in Serum After Excision of Breast Tumor," *Anticancer Res.* 9:437–440, 1989.

Eskelinen et al., "A New Tumor Marker MCA in breast Cancer Diagnosis," *Anticancer Res.* 8:665–668, 1988.

Fulkerson et al., "Artificial Induction of Lactation in Ewes: The Involvement of Progesterone and Prolactin in Lactogenesis," *Aust. J. Biol. Sci.* 29:357–363, 1976.

Gordon and Cross, "An Enzyme–linked Immunosorbent Assay for Cancer Procoagulant and Its Potential as a New Tumor Marker," *Cancer Res.* 50:6229–6234, 1990.

Greiner, "Tumor Markers," *Pharm. Tech.*, May, 1993.

Hayes, "Tumor markers for breast cancer," *Anals of Oncology* 4:807–819, 1993.

Hou et al., "A Simple Method of duct Cannulation and Localization for Galactography before Excision in Patients with Nipple Discharge," *Radiology* 195:568–569, 1995.

Inaji et al., "Carcinoembryonic antigen Estimation in Nipple Discharge as an Adjunctive Tool in the Diagnosis of Early Breast Cancer," *Cancer* 60:3008–3013, 1987.

Ingelman–Sundberg et al., "Immunocytochemical reactivity of breast cancer tissue with antibodies to neuron–specific enolase and an adenocarcinoma–associated glycolipid antigen," *Virchows Archiv. A Pathol. Anta.* 415:539–544, 1989.

Kawamoto, "Breast Cancer Diagnosis by Lactage Dehydrogenase Isozymes in Nipple Discharge," *Cancer* 73:1836–1841, 1994.

Molinolo et al., "Enhanced Tumor Binding Using Immunohistochemical Analyses by second Generation anti–Tumor––associated Glycoprotein 72 Monoclonal Antibodies Versus Monoclonal Antibody B72.3 in Human Tissue," *Cancer Res.* 50:1291–1298, 1990.

Mori et al., "Evaluation of Dot–immunobinding Assay for Carcinoembryonic Antigen Determination in Nipple discharge as an Adjunct in the Diagnosis of Early Breast Cancer," *Jpn. J. Clin. Oncol.* 19:373–379, 1989.

Nagle et al., "Characterization of Breast Carcinomas by Two Monoclonal Antibodies Distinguishing Myoepithelial from Luminal Epithelial Cells," *J. Histochem. and Cytochem* 34(7):869–881, 1986.

North et al., "Vasopressin gene related products are markers of human breast cancer," *Breast Cancer Research and Treatment* 34:229–235, 1995.

Physicians Desk Reference, 49th Edition, p. 2193, 1995.

Porter–Jordan and Lippman, "Overview of the Biological Markers of Breast Cancer," *Breast Cancer* 8:73–100, 1994.

Rakhimberdiev, *Izv. Akad. Nauk.Kaz. SSR Ser. Biol.* 4:64, 1980.

Roche, "Immunohistochemical Stains for Breast Cancer," *Mayo Clin. Proc.* 69:57–58, 1994.

Rose, "Hormones and Growth Factors in Nipple Aspirates from Normal Women and Benign Breast Disease Patients," *Cancer Detection and Prevention* 16:43–51, 1992.

Rosner et al., "Diagnosis of Breast Carcinoma with Radiolabeled monoclonal Antibodies (MoAbs) to Carcinoembryonic antigen (CEA) and Human Milk Fat Globulin (HMFG)," *Cancer Invest.* 13(6):573–582, 1995.

Sauter et al., "Nipple aspirate fluid: a promising non–invasive method to identify cellular markers of breast cancer risk," *British J. of Cancer* 76(4):494–501, 1997.

Sheahan et al., "Differential Reactivities of Carcinoembryonic Antigen (CEA) and CEA–Related Monoclonal and Polyclonal Antibodies in Common Epithelial Malignancies," *A.j.C.P.* 94:157–164, 1990.

Vetvicka et al., "Human Breast Milk Contains Procathepsin D—Detection by Specific Antibodies," *Biochemistry and Molecular Biology International* 30(5):921–928, 1993.

Focus, Harvard University News Office, Mar.21, 1991, pp. 2–3.

* cited by examiner

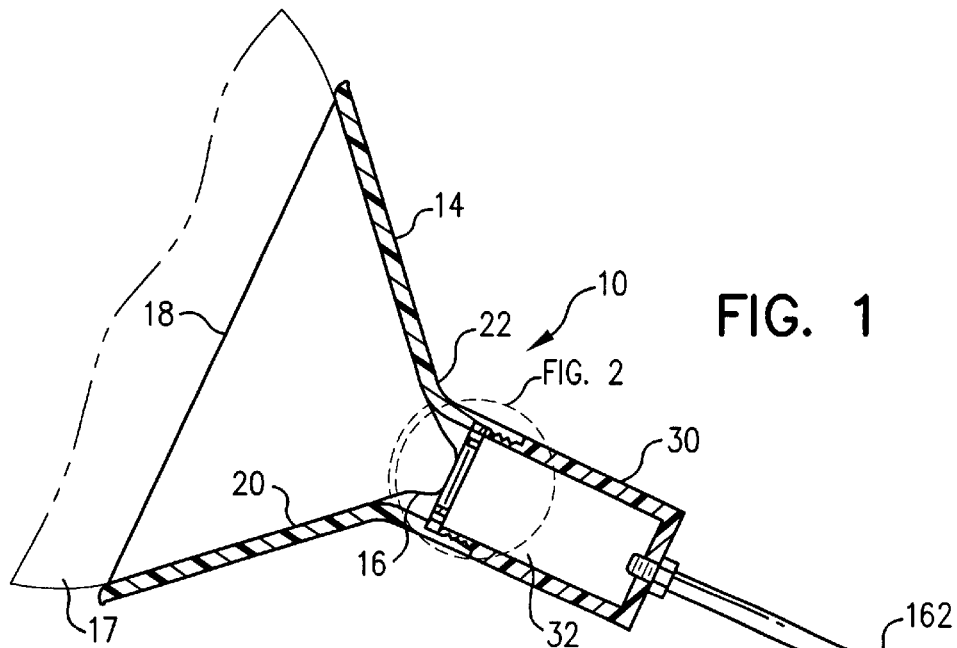
FIG. 1
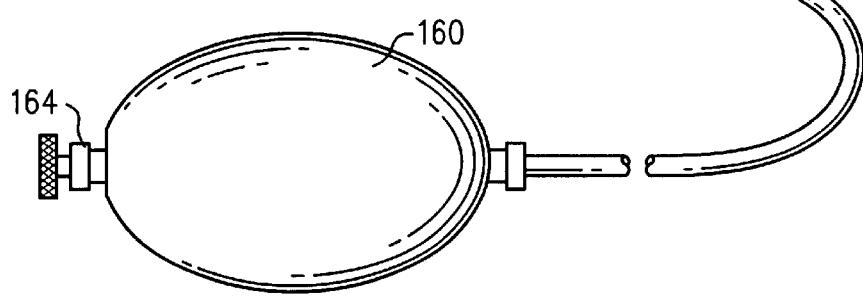
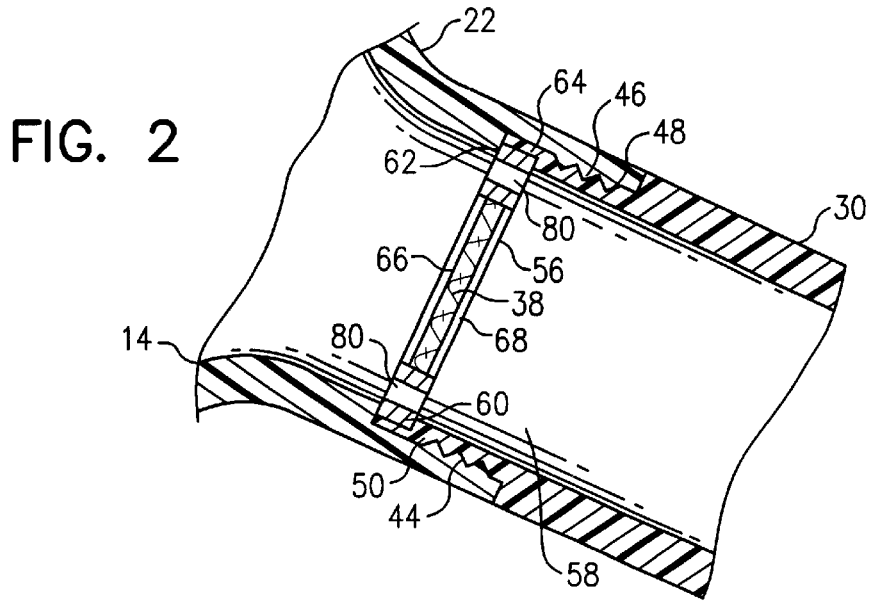
FIG. 2

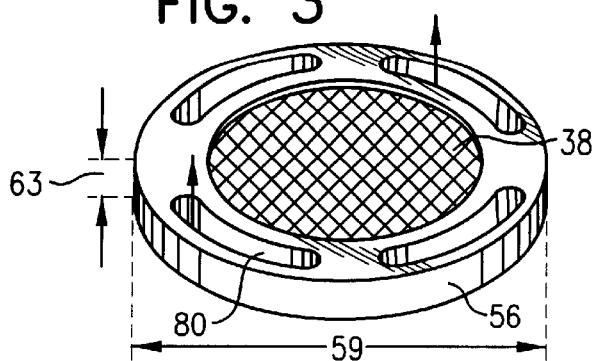
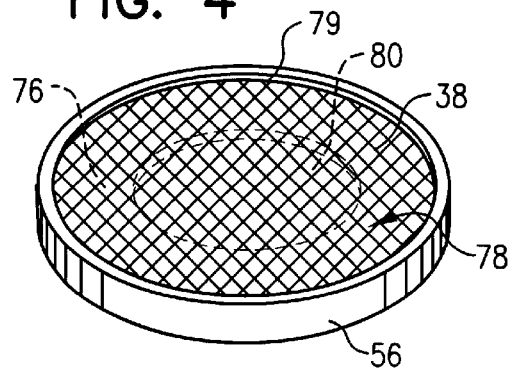
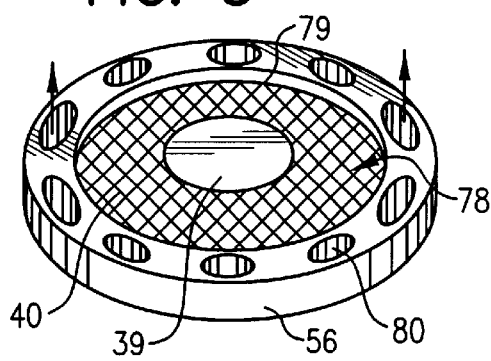
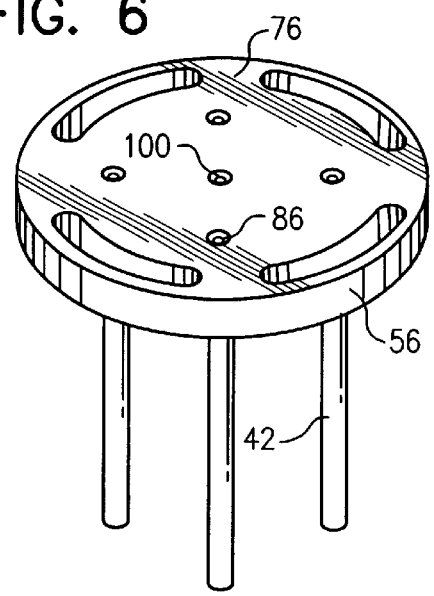
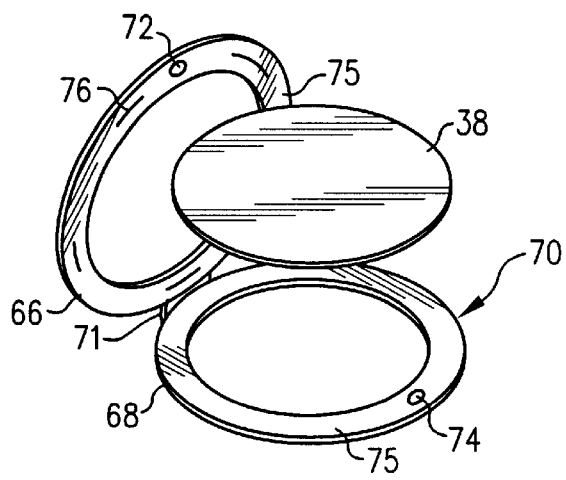

METHODS AND DEVICES FOR OBTAINING AND ASSAYING MAMMARY FLUID SAMPLES FOR EVALUATING BREAST DISEASES, INCLUDING CANCER

RELATED APPLICATIONS

This application is a continuation-in-part of and claims the benefit of U.S. patent application Ser. No. 08/709,207 filed Aug. 27, 1996, now U.S. Pat. No. 5,798,266, issued Aug. 25, 1998.

TECHNICAL FIELD

The invention relates to methods, devices, and kits for obtaining and assaying biological samples from mammary fluid. More specifically, the invention relates to methods, devices, and kits for obtaining and assaying fluid and cytological samples from the mammary glands of a mammalian subject for evaluating, diagnosing and managing breast disease, including infections, pre-cancerous conditions, cancer susceptibility and cancer.

BACKGROUND OF THE INVENTION

Breast cancer is by far the most common form of cancer in women, and is the second leading cause of cancer death in humans. Despite many recent advances in diagnosing and treating breast cancer, the prevalence of this disease has been steadily rising at a rate of about 1 k per year since 1940. Today, the likelihood that a women living in North America will develop breast cancer during her lifetime is one in eight.

The current widespread use of mammography has resulted in improved detection of breast cancer. Nonetheless, the death rate due to breast cancer has remained unchanged at about 27 deaths per 100,000 women. All too often, breast cancer is discovered at a stage that is too far advanced, when therapeutic options and survival rates are severely limited. Accordingly, more sensitive and reliable methods are needed to detect small (less than 2 cm diameter), early stage, in situ carcinomas of the breast. Such methods should significantly improve breast cancer survival, as suggested by the successful employment of Papinicolou smears for early detection and treatment of cervical cancer.

In addition to the problem of early detection, there remain serious problems in distinguishing between malignant and benign breast disease, in staging known breast cancers, and in differentiating between different types of breast cancers (eg. estrogen dependent versus non-estrogen dependent tumors). Recent efforts to develop improved methods for breast cancer detection, staging and classification have focused on a promising array of so-called cancer "markers." Cancer markers are typically proteins that are uniquely expressed (eg. as a cell surface or secreted protein) by cancerous cells, or are expressed at measurably increased or decreased levels by cancerous cells compared to normal cells. Other cancer markers can include specific DNA or RNA sequences marking deleterious genetic changes or alterations in the patterns or levels of gene expression associated with particular forms of cancer.

A large number and variety of breast cancer markers have been identified to date, and many of these have been shown to have important value for determining prognostic and/or treatment-related variables. Prognostic variables are those variables that serve to predict disease outcome, such as the likelihood or timing of relapse or survival. Treatment-related variables predict the likelihood of success or failure of a given therapeutic plan. Certain breast cancer markers clearly serve both functions. For example, estrogen receptor levels are predictive of relapse and survival for breast cancer patients, independent of treatment, and are also predictive of responsiveness to endocrine therapy. Pertschuk et al., *Cancer* 66: 1663–1670, 1990; Parl and Posey, *Hum. Pathol.* 19: 960–966, 1988; Kinsel et al., *Cancer Res.* 49: 1052–1056, 1989; Anderson and Poulson *Cancer* 65: 1901–1908, 1989.

The utility of specific breast cancer markers for screening and diagnosis, staging and classification, monitoring and/or therapy purposes depends on the nature and activity of the marker in question. For general reviews of breast cancer markers, see Porter-Jordan et al., *Hematol. Oncol. Clin. North Amer.* 8: 73–100, 1994; and Greiner, *Pharmaceutical Tech., May,* 1993, pp. 28–44. As reflected in these reviews, a primary focus for developing breast cancer markers has centered on the overlapping areas of tumorigenesis, tumor growth and cancer invasion. Tumorigenesis and tumor growth can be assessed using a variety of cell proliferation markers (for example Ki67, cyclin D1 and proliferating cell nuclear antigen (PCNA)), some of which may be important oncogenes as well. Tumor growth can also be evaluated using a variety of growth factor and hormone markers (for example estrogen, epidermal growth factor (EGF), erbB-2, transforming growth factor (TGF), which may be overexpressed, underexpressed or exhibit altered activity in cancer cells. By the same token, receptors of autocrine or exocrine growth factors and hormones (for example insulin growth factor (IGF) receptors, and EGF receptor) may also exhibit changes in expression or activity associated with tumor growth. Lastly, tumor growth is supported by angiogenesis involving the elaboration and growth of new blood vessels and the concomitant expression of angiogenic factors that can serve as markers for tumorigenesis and tumor growth.

In addition to tumorigenic, proliferation and growth markers, a number of markers have been identified that can serve as indicators of invasiveness and/or metastatic potential in a population of cancer cells. These markers generally reflect altered interactions between cancer cells and their surrounding microenvironment. For example, when cancer cells invade or metastasize, detectable changes may occur in the expression or activity of cell adhesion or motility factors, examples of which include the cancer markers Cathepsin D, plasminogen activators, collagenases and other factors. In addition, decreased expression or overexpression of several putative tumor "suppressor" genes (for example nm23, p53 and rb) has been directly associated with increased metastatic potential or deregulation of growth predictive of poor disease outcome.

Additional representative breast disease markers within these various classes include prostaglandin E2 (PGE2); estrogen-regulated proteins such as pS2; interleukins (eg., IL-10); S-100 protein; vimentin; epithelial membrane antigen; prostate specific antigen (PSA); bcl-2; CA15-3 (an aberrant form of polymorphic epithelial mucin (PEM)); CA 19-9; mucin core carbohydrates (eg., Tn antigen and Tn-like antigens); alpha-lactalbumin; lipid-associated sialic acid (LASA); galactose-N-acetylgalactosamine (Gal-GalNAC); GCDFP-15; Le(y)-related carbohydrate antigen; CA 125; urokinase-type plasminogen activator (uPA) and uPA related antigens and complexes (eg., LMW-uPA, HMW-uPA, uPA aminoterminal fragment (ATF), uPA receptor (uPAR) and complexes with inhibitors such as PAl-1 and PAl-2); beta-glucuronidase; CD31; CD44 splice variants; blood group antigens (eg., ABH, Lewis, and MN); and genetic lesions or altered expression levels of CCND1, EMS1, BRCA1 and BRCA2 genes.

In summary, the evaluation of proliferation markers, oncogenes, growth factors and growth factor receptors, angiogenic factors, proteases, adhesion factors and tumor suppressor genes, among other cancer markers, can provide important information concerning the risk, presence, status or future behavior of cancer in a patient. Determining the presence or level of expression or activity of one or more of these cancer markers can aid in the differential diagnosis of patients with uncertain clinical abnormalities, for example by distinguishing malignant from benign abnormalities.

Furthermore, in patients presenting with established malignancy, cancer markers can be useful to predict the risk of future relapse, or the likelihood of response in a particular patient to a selected therapeutic course. Even more specific information can be obtained by analyzing highly specific cancer markers, or combinations of markers, which may predict responsiveness of a patient to specific drugs or treatment options.

Methods for detecting and measuring cancer markers have been recently revolutionized by the development of immunological assays, particularly by assays that utilize monoclonal antibody technology. Previously, many cancer markers could only be detected or measured using conventional biochemical assay methods, which generally require large test samples and are therefore unsuitable in most clinical applications. In contrast, modern immunoassay techniques can detect and measure cancer markers in relatively much smaller samples, particularly when monoclonal antibodies that specifically recognize a targeted marker protein are used. Accordingly, it is now routine to assay for the presence or absence, level, or activity of selected cancer markers by immunohistochemically staining breast tissue specimens obtained via conventional biopsy methods. Because of the highly sensitive nature of immunohistochemical staining, these methods have also been successfully employed to detect and measure cancer markers in smaller, needle biopsy specimens which require less invasive sample gathering procedures compared to conventional biopsy specimens. In addition, other immunological methods have been developed and are now well known in the art which allow for detection and measurement of cancer markers in non-cellular samples such as serum and other biological fluids from patients. The use of these alternative sample sources substantially reduces the morbidity and costs of assays compared to procedures employing conventional biopsy samples, which allows for application of cancer marker assays in early screening and low risk monitoring programs where invasive biopsy procedures are not indicated.

For the purpose of breast cancer evaluation, the use of conventional or needle biopsy samples for cancer marker assays is often undesirable, because a primary goal of such assays is to detect the cancer before it progresses to a palpable or mammographically detectable tumor stage. Prior to this stage, biopsies are generally contraindicated, making early screening and low risk monitoring procedures employing such samples untenable. Therefore, there is general need in the art to obtain samples for breast cancer marker assays by less invasive means than biopsy, for example by serum withdrawal.

Efforts to utilize serum samples for breast cancer marker assays have met with limited success, largely because the targeted markers are either not detectable in serum, or because telltale changes in the levels or activity of the markers cannot be monitored in serum. In addition, the presence of breast cancer markers in serum probably occurs at the time of micro-metastasis, making serum assays less useful for detecting pre-metastatic disease. In contrast, fluid within the mammary glands themselves is expected to contain much higher and more biologically relevant levels of breast cancer markers than serum, particularly in view of the fact that 80%–90% of all breast cancers occur within the intraductal epithelium of these glands. Fluid within the breast ducts is expected to contain an assemblage and concentration of hormones, growth factors and other potential markers comparable to those secreted by, or acting upon, the surrounding cells of the alveolar-ductal system. Likewise, mammary fluid is expected to contain cells and solid cellular debris or products that can be used in cytological or immunological assays to evaluate intracellular or cell surface markers that may not be detectable in the liquid fraction of mammary fluid.

Previous attempts to develop non-invasive breast cancer marker assays utilizing mammary fluid samples have included studies of mammary fluid obtained from patients presenting with spontaneous nipple discharge. In one of these studies, conducted by Inaji et al., *Cancer* 60: 3008–3013, 1987, levels of the breast cancer marker carcinoembryonic antigen (CEA) were measured using conventional, enzyme linked immunoassay (ELISA) and sandwich-type, monoclonal immunoassay methods.

These methods successfully and reproducibly demonstrated that CEA levels in spontaneously discharged mammary fluid provide a sensitive indicator of nonpalpable breast cancer. In a subsequent study, also by Inaji et al., *Jpn. J. Clin. Oncol.* 19: 373–379, 1989, these results were expanded using a more sensitive, dry chemistry, dot-immunobinding assay for CEA determination. This latter study reported that elevated CEA levels occurred in 430 of patients tested with palpable breast tumors, and in 73% of patients tested with nonpalpable breast tumors. CEA levels in the discharged mammary fluid were highly correlated with intratumoral CEA levels, indicating that the level of CEA expression by breast cancer cells is closely reflected in the mammary fluid CEA content. Based on these results, the authors concluded that immunoassays for CEA in spontaneously discharged mammary fluid are useful for screening nonpalpable breast cancer.

Although the evaluation of mammary fluid has been shown to be a useful method for screening nonpalpable breast cancer in women who experience spontaneous nipple discharge, the rarity of this condition renders the methods of Inaji et al, inapplicable to the majority of women who are candidates for early breast cancer screening. In addition, the first Inaji report cited above determined that certain patients suffering spontaneous nipple discharge secrete less than 10 $\mu$l of mammary fluid, which is a critically low level for the ELISA and sandwich immunoassays employed in that study. It is likely that other antibodies used to assay other cancer markers may exhibit even lower sensitivity than the anti-CEA antibodies used by Inaji and coworkers, and may therefore not be adaptable or sensitive enough to be employed even in dry chemical immunoassays of small samples of spontaneously discharged mammary fluid.

In view of the above, an important need exists in the art for more widely applicable, non-invasive methods and materials to obtain biological samples for use in evaluating, diagnosing and managing breast disease including cancer, particularly for screening early stage, nonpalpable breast tumors. A related need exists for methods and materials that utilize such readily obtained biological samples to evaluate, diagnose and manage breast disease, particularly by detecting or measuring selected breast cancer markers, or panels of breast cancer markers, to provide highly specific, cancer prognostic and/or treatment-related information, and to diagnose and manage pre-cancerous conditions, cancer susceptibility, breast infections and other breast diseases.

SUMMARY OF THE INVENTION

It is therefore an object of the present invention to provide non-invasive methods and kits for obtaining biological samples that can be employed in assays for evaluating, diagnosing and managing breast disease, particularly cancer.

It is a further object of the invention to achieve the above object in assay methods and kits that are widely applicable to a broad range of patients, and that include useful assays and kits for screening early stage, nonpalpable mammary tumors.

It is yet another object of the invention to provide methods and kits that utilize the aforementioned biological samples to evaluate, diagnose and manage breast disease, preferably breast cancer, by detecting and/or measuring selected breast disease markers such as breast cancer markers, or panels of breast cancer markers, to provide highly specific prognostic and/or treatment-related information to the clinician.

The invention achieves these objects and other objects and advantages that will become apparent from the description which follows by providing non-invasive methods for obtaining biological samples from a mammary organ of a mammalian patient. Specifically, the methods of the invention involve administering oxytocin or an oxytocin analog to a mammalian patient in an amount that is effective to stimulate expression of mammary fluid from a nipple of the patient. The oxytocin is preferably administered intranasally and is allowed to reach a target alveolar-ductal tissue of the breast where the oxytocin stimulates myoepithelial contraction of the alveolar-ductal tissue. Alternatively, an intramuscular or intravascular injection of oxytocin can effect the same myoepithelial contraction response as the intranasal administration route.

The amount, timing and/or mode of oxytocin administration may be adjusted on an individual basis depending on such factors as menstrual cycle stage, use of birth control or hormone replacement therapy, pregnancy history, age of onset of menarch, enthnicity and other factors known to affect an individual's propensity for breast fluid expression.

A mammary fluid collector, preferably a breast pump, is then optionally applied to the nipple and is used to receive the expressed breast fluid. In preferred methods involving use of a breast pump, negative pressure is generated on the breast to facilitate the oxytocin stimulated expression of mammary fluid. Alternatively, the mammary fluid can be expressed and collected without the aid of a breast pump, which may require an increase of oxytocin dosage or lengthening of the post administration time period before breast fluid is fully expressed from the nipple.

During or after the mammary fluid expression step, a biological sample is collected from the expressed mammary fluid, which sample may consist of whole mammary fluid, whole cells, cell fragments, cell membranes, selected liquid, cellular or other solid fractions of the mammary fluid, as well as proteins, glycoproteins, peptides, nucleotides (including DNA and RNA polynucleotides) and other like biochemical and molecular constituents of the mammary fluid.

Sample collection can be achieved simply by receiving the expressed mammary fluid within any suitable reservoir, such as an ordinary sample storage container or assay vessel. In preferred embodiments of the invention, the expressed mammary fluid is exposed to a solid phase sample collection medium, simultaneous with or subsequent to the time of breast fluid expression. Suitable solid phase media in this context include microscopic glass slides, capillary tubes, coated tubes, microtiter wells or plates, membranes, filters, affinity columns, dot blot matrices, beads, microspheres, resins, and other like media that will selectively adsorb, bind, filter, partition or otherwise process desired components of the mammary fluid for convenient incorporation into a desired assay. Often it will be desirable to combine a plurality of solid phase media for sample collection, eg., a filter and membrane, a membrane and a particulate medium, etc., for example to differentially partition and adsorb selected components of the breast fluid. In conjunction with sample collection, the sample may be exposed to other agents such as buffers, diluents, extraction or chromatographic media, cross-linking agents, denaturing agents, etc., to stabilize or otherwise prepare the sample for processing within a desired assay.

Also provided within the invention are methods and devices for obtaining a biological sample from a patient and/or determining the amount of a breast disease marker in a biological sample from breast fluid which employ a novel breast pump or breast pump adapter. The breast pump functions in a similar fashion as a conventional breast pump but also provides a solid phase sample collection medium in fluid connection with the pump. The solid phase sample collection medium may be integrated within the breast pump or otherwise fluidly connected therewith, so that a sample of expressed breast fluid contacts the collection medium while the pump remains applied to the breast.

In related aspects of the invention, methods are provided for determining the presence or amount of a breast disease marker, preferably a breast cancer marker, in biological samples obtained from a mammary organ of a mammalian patient. These methods involve intranasal, intramuscular or intravascular administration of oxytocin or an oxytocin analog to mammalian patients in amounts effective to stimulate mammary fluid expression in the patient. Once a sufficient post-administration time period has elapsed to allow the oxytocin to reach and stimulate target alveolar-ductal tissues, mammary fluid is collected directly from the nipple or, alternatively, the breast is pumped, and a biological sample from expressed mammary fluid is collected, as above. After the sample is collected a bioassay is conducted on the sample to determine the presence and/or amount of the breast disease marker in the sample. Suitable bioassays in this regard include assays to detect known markers of breast disease, such as assays employing immunological or other suitable probes to detect specific antigens and other markers expressed by selected pathogens, including bacterial and viral pathogens. More preferred bioassays will detect individual markers or panels of markers of benign breast tumors, pre-cancerous breast disease, and/or breast cancer, such as assays employing immunological or other suitable probes to detect specific antigens and other markers expressed by benign, pre-cancerous and/or cancerous alveolar-ductal cells of the breast. Preferably, the assay will detect the presence or amount of multiple breast disease markers in the biological sample, for example by including a panel of immunological or molecular probe(s) that bind or react with multiple breast cancer markers.

In yet additional aspects of the invention, clinically useful kits are provided for determining the presence and/or amount of a breast disease marker, preferably a breast cancer marker, in biological samples obtained from a mammary organ of a mammalian patient. The kits include a pharmaceutical preparation of oxytocin in a biologically suitable carrier. Preferably, the oxytocin preparation is a solution of oxytocin provided in an intranasal spray applicator. The kits also preferably include a collecting device for collecting a biological sample from the expressed mammary fluid, which collecting device may range from a simple fluid reservoir to solid phase media that can be directly incorporated into solid phase bioassays. In this context, an optional breast pump or breast pump adapter may also be provided serving a dual purpose of applying negative pressure to the breast to facilitate mammary fluid expression from the nipple following oxytocin stimulation, and to provide a solid phase sample collection medium in fluid connection with the breast pump for biological sample collection.

In particularly preferred embodiments of the invention, kits include compositions and/or devices for detecting the presence or amount of one or more breast disease marker(s) in the biological sample, for example one or more immunological or molecular probe(s) that binds or reacts with one or more breast cancer marker(s).

BRIEF DESCRIPTION OF THE DRAWINGS

FIG. 1 is a partial sectional view of a breast pump employing the concepts of the invention.

FIG. 2 is a sectional view of a portion of the breast pump as indicated in FIG. 1.

FIG. 3 is a perspective view of a support member for supporting a solid phase sample collection medium in fluid connection with a breast pump.

FIG. 4 is a perspective view of an alternative support member for supporting a solid phase sample collection medium in fluid connection with a breast pump.

FIG. 5 is a perspective view of an alternative support member for supporting a solid phase sample collection medium in fluid connection with a breast pump.

FIG. 6 is a perspective view of an alternative support member for supporting a solid phase sample collection medium in fluid connection with a breast pump.

FIG. 7 is a perspective view of an alternative support member for supporting a solid phase sample collection medium in fluid connection with a breast pump.

DETAILED DESCRIPTION OF THE INVENTION

Figure 8:
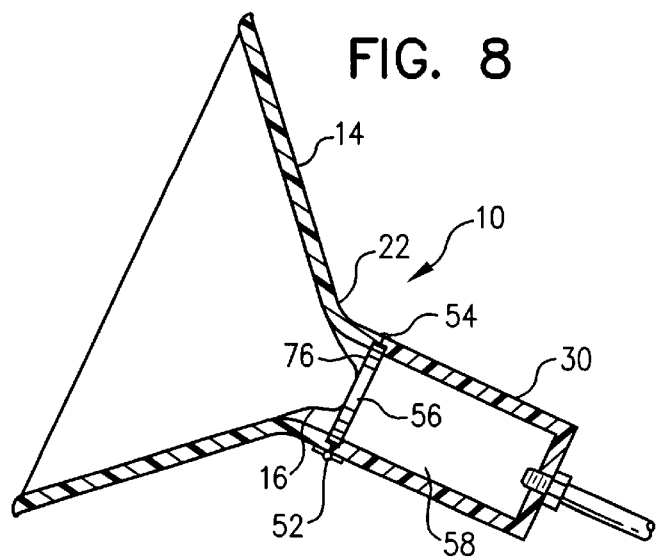
FIG. 8 is a sectional view of a breast pump device employing the concepts of the invention.

As noted above, the invention provides methods for obtaining biological samples from mammary fluid. Preferably, these methods are non-invasive, meaning they are non-surgical and do not involve penetration of the breast by needles or other intrusive devices. To achieve a non-invasive sample collecting method, the invention relies specifically on administering the peptide hormone oxytocin to a mammalian patient, in an amount that is effective to stimulate expression of mammary fluid from a nipple of the patient when a breast pump is applied to the nipple to assist the mammary fluid expression. Preferably the oxytocin preparation is administered intranasally and is administered in an amount that is intranasally effective to stimulate expression of mammary fluid from the nipple.

Oxytocin is a peptide hormone of pituitary origin which is naturally released into the bloodstream of lactating women in response to suckling, and stimulates contraction of myoepithelial cells in the mammary alveoli and ducts to cause milk ejection. Cobo. *J. Perinat. Med.* 21: 77–85, 1993. The drug has also been widely used for stimulating labor in pregnant women, due to its activity of stimulating uterine contractions. Satin et al., *Am. J. Obstet. Gynecol.* 166: 1260–1261, 1992. For these reasons, the pharmacology of oxytocin has been thoroughly investigated, including detailed studies of effective dosages, half-life and potential side effects.

For use in the present invention, an oxytocin preparation is provided for intranasal, intramuscular, or intravenous administration that contains oxytocin in a biologically suitable, liquid carrier. As used herein, "oxytocin" refers to natural or synthetic oxytocin and biologically active derivatives and analogs thereof. Naturally occuring oxytocin from mammalian sources is of course suitable, as are other known, naturally occuring oxytocin-like peptide analogues and their synthetic counterparts having similar activities for stimulating alveolar-ductal myoepithelial contraction.

Preferably, the oxytocin used within the invention is a simple peptide hormone comprising a cyclic peptide, the peptide having a well defined ring portion (Cys-Tyr-Ile-Gln-Asn-Cys) and tail portion (Pro-Leu-Gly). However, numerous derivatives and analogues are known, or readily obtainable, in the art, eg., derivatives or analogues having amino acid truncations, deletions or substitutions at one or more residues of the peptide and which exhibit substantially the same activity as naturally occurring oxytocin (i.e., having at least 75%, and preferably 85%–95% or more, activity compared to that of native oxytocin for stimulating alveolar-ductal myoepithelial contraction). The most economic oxytocin preparations for use within the invention contain a synthetic oxytocin (eg. PITOCIN® or SYNTOCINON® available from various providers, for example Sandoz (Basel, Switzerland) and United States Pharmacopeia. For use in the methods and kits of the invention, a preferred oxytocin preparation contains approximately 40 USP units of oxytocin per ml of liquid carrier. Preferred liquid carriers are biologically compatible solutions, such as a lactated Ringer's solution or other physiologically balanced, sterile, non-toxic and non-irritative solution. To administer the oxytocin intranasally, a standard nasal squeeze bottle is used, which delivers approximately 0.5 ml of the oxytocin preparation into the patient's nostril when squeezed. The oxytocin is absorbed by the nasal mucosa into the systemic circulation where it reaches and acts specifically on the myoepithelial cells surrounding the alveoli of the breast and making up the walls of the lactiferous ducts, causing their smooth muscle fibers to contract and force any fluids present into the large ducts or sinuses where it can be expressed from the nipple spontaneously onto a sample collector or by the further action of a breast pump. Intranasal application of the spray preparation is therefore a practical and effective method of administration. The half-life of oxytocin in the human bloodstream is extremely short, estimated to be about 10–15 minutes or less, due to its rapid removal from plasma by the kidney, liver, and mammary gland, and the time to pharmacokinetic and clinical steady state is readily determined depending on the mode of administration (eg. bolus dosage, repeat administration, or steady infusion). (See for example, Gonser, *Arch. Gynecol. Obstet.* 256: 63–66, 1995; and Orhue, *Obstet. Gynecol.* 83: 229–233, 1994, each incorporated herein by reference in its entirety). It is therefore a routine matter to determine an appropriate concentration and dose of the oxytocin preparation to administer an effective amount (either intranasally effective, intravenously effective, or intramuscularly effective) of the oxytocin to cause expression of mammary fluid with or without the assistance of a breast pump. (See for example, Newton, *Ann. N.Y. Acad. Sci.* 652: 481–483; Mena, *Neuroendocrinoloqy* 61: 722–730, 1995; Gonser, *Arch. Gynecol. Obstet.* 256: 63–66, 1995; Orhue, Obstet. *Gynecol.* 83: 229–233, 1994; Satin et al., *Am. J. Obstet. Gynecol.,* 166: 1260–1261, 1992; and Satin et al., *Obstet. Gynecol.* 83: 234–238, 1994, each incorporated herein by reference in its entirety).

Although not all female patients are expected to be responsive to intranasal oxytocin stimulation, an intranasally effective amount of oxytocin for the purposes of the invention can be readily determined. As used herein, an intranasally effective amount of oxytocin is an amount of oxytocin sufficient to intranasally stimulate the expression of at least 3 $\mu$l of mammary fluid in at least 500 of non-lactating female patients with the aid of negative pressure to the nipple of between 50–200 mm Hg applied by a breast pump up to 45 min after a first administration of the oxytocin spray. It may be necessary, and indeed preferred, to administer a low, preliminary dose of oxytocin to the patient, for example a single spray of a 40 Unit/ml oxytocin solution in each nostril, or multiple sprays of a lower concentration oxytocin preparation, and thereafter wait to determine a particular patient's sensitivity. If there is no reaction with an initial application of the breast pump after a short post-administration period of 2–15 minutes, and preferably 2–5 minutes, a booster dose of the oxytocin spray may be administered and the pump reapplied. In this way, the clinician can modulate the dosage to each patient's varying sensitivity, and thereby minimize potential adverse side effects. Alternatively, an effective dose of intramuscular or intravenous oxytocin can be used according to the same dosage determination and administration principles in patients where intranasal administration fails or is otherwise contra-indicated as a preferred mode of administration.

As noted above, the amount, timing and/or mode of oxytocin administration may be adjusted based on specific factors known to render individuals more or less sensitive to induction of breast fluid expression. These factors are generally well known in the art, and include, for example, menstrual cycle stage, use of birth control or hormone replacement therapy, pregnancy history, age of onset of menarch, and enthnicity, among other factors.

Thus, in one aspect of the invention, methods for obtaining a biological sample from a patient and/or determining the amount of a breast disease marker in a biological sample from breast fluid are provided which include a step of determining a menstrual stage of the patient. Based on the determined menstrual stage, a drug administration protocol is selected having a predetermined oxytocin dosage, timing and/or frequency of oxytocin delivery, and/or mode of oxytocin administration.

According to these methods, one or more variables of oxytocin dosage, timing and/or frequency of oxytocin delivery, and/or mode of oxytocin administration are selected depending on whether the patient is staged within one of five approximate menstrual phases. These phases include 1) a proliferative phase (characterized by a tight configuration of the alveolar lumena); 2) a follicular phase (characterized by a defined configuration of the alveolar lumena); 3) a luteal phase (characterized by an open configuration of the alveolar lumena, with some secretion by the alveolar cells); 4) a secretory phase (characterized by an open configuration of the alveolar lumena, with secretion by the alveolar cells); and 5) a menstrual phase (characterized by a distended configuration of the alveolar lumena, with secretion by the alveolar cells).

It is generally not desired to conduct the methods of the invention for patients staged in the proliferative or follicular stage of their menstrual cycle (approximately 3–7 days and 8–14 days, respectively). However, in some circumstances sample collection can be performed for these individuals using high and/or repetitive doses of oxytocin and otherwise optimizing the breast fluid expression response by selecting a particular mode of oxytocin administration, or combination thereof (eg., intravenous administration followed by intranasal administration). For patients staged in the luteal or secretory stage of their menstrual cycle (approximately 15–20 days and 21–27 days, respectively), intermediate dosages of oxytocin are selected and repetitive administrations are reduced or eliminated. For patients staged in the menstrual phase, dosages of oxytocin and repetitive administrations are reduced even further while still providing an effective administration protocol to yield sufficient breast fluid expression.

Determination of effective administration protocols for patients of different menstrual stages can also be readily achieved within the invention. As used herein, an effective administration protocol yields at least 3 $\mu$l of expressed mammary fluid in at least 50% of non-lactating female patients at an equivalent menstrual stage with the aid of negative pressure to the nipple of between 50–200 mm Hg applied by a breast pump up to 45 min after a first administration of the oxytocin spray. Various combinations of oxytocin dosage, timing and/or frequency of oxytocin delivery, and/or mode of oxytocin administration are contemplated, as can be readily determined by the skilled artisan in accordance with the teachings herein. Likewise, it will often be preferred to administer a low, preliminary dose of oxytocin to the patient and thereafter wait to determine a particular patient's sensitivity, even when an individual's menstrual stage has been determined and a particular administration protocol selected. Thus, if there is no reaction with an initial application of the breast pump after a short post-administration period, a booster dose of the oxytocin may be administered and the pump reapplied. In this way also, the clinician can apply a first, stage specific dose of oxytocin and thereafter modulate the dosage, period of time between booster administrations, and/or mode of administration, to each patient's varying sensitivity.

In other, related aspects of the invention, methods for obtaining a biological sample from a patient and/or determining the amount of a breast disease marker in a biological sample from breast fluid are provided which include a step of determining a non-menstrual stage patient sensitivity index. Examples of such indices include 1) patient use of hormone based birth control; 2) patient use of hormone replacement therapy; 3) patient pregnancy history; 4) patient age of onset of menarch; and 5) patient enthnicity. Other indices associated with sensitivity to induction of breast fluid expression are also contemplated. These factors can be determined by such routine steps as patient consultation, evaluation of patient records, and clinical or laboratory-based analysis (eg., physical screening, measurement of sex-steroid hormone levels, etc.) Based on a determined non-menstrual stage sensitivity index, an effective drug administration protocol is selected having a predetermined oxytocin dosage, timing and/or frequency of oxytocin delivery, and/or mode of oxytocin administration, in accordance with the methods described above. In yet additional methods an effective drug administration protocol is selected by first determining both a patient's menstrual stage and at least one non-menstrual stage sensitivity index specific to the patient, and thereafter selecting an effective oxytocin administration protocol based on these combined indices.

In yet additional methods within the invention, it may be preferred to conduct the foregoing sample collection methods in conjunction with a conventional mammographic procedure. In this manner, costs, time and patient discomfort can be minimized. Further, by conducting the sample collection immediately following a mammogram it is expected that breast fluid expression may be facilitated by breast manipulation during the initial procedure. Additional steps to facilitate breast fluid expression include manual breast massage and application of heat packs to the breast.

Once an effective dose(s) of oxytocin is administered and the clinician has allowed a suitable post-administration period to elapse for the oxytocin to reach and stimulate the target alveolar-ductal tissue, the breast pump is applied according to well known procedures and negative pressure is generated on the breast to facilitate the expression of mammary fluid. Within the methods of the invention, negative pressures of 50–200 mm Hg are preferred, and these pressures are maintained, preferably intermittently, for approximately 1–15 minutes, depending on the sensitivity of individual patients, oxytocin dosage and other factors. Alternatively, mammary fluid expression can be achieved without the aid of the breast pump using a separate sample collector to receive the expressed breast fluid, as described herein.

The volume of expressed mammary fluid will vary depending on a variety of factors, including patient sensitivity to oxytocin, dosage of oxytocin delivered, time and pressure of breast pump administration, and other factors. For the least sensitive breast marker assays of the invention, a volume of expressed mammary fluid of 300–500 $\mu$l is preferred to provide ample material for conducting the assay, and these volumes will be obtainable from a substantial proportion of women treated according to the above methods. To express 300–500 $\mu$l of mammary fluid, some women will require repeated stimulation treatments, perhaps requiring pooling of mammary fluid samples obtained during multiple patient visits. However, for more sensitive assays of the invention, eg. solid phase immunoassays, much smaller samples of 3 $\mu$l or less will be suitable to carry out the assays, particularly in the case of breast cancer markers that are naturally secreted into the mammary fluid and are therefore expected to be present in very high concentrations compared to, for example, breast epithelial cell surface antigens or intracellular antigens that are not secreted.

During or after the mammary fluid expression step, a biological sample is collected from the expressed mammary fluid. A range of suitable biological samples are contemplated and will be useful within the methods of the invention, including whole mammary fluid, selected liquid or solid fractions of the mammary fluid, whole cells or cellular constituents, proteins, glycoproteins, peptides, nucleotides (including DNA and RNA polynucleotides) and other like biochemical and molecular constituents of the mammary fluid. Sample collection can be achieved simply by receiving the expressed mammary fluid within a suitable reservoir, such as an ordinary sample storage container or assay vessel.

In preferred embodiments of the invention, the expressed mammary fluid is contacted with a solid phase sample collection medium, simultaneous with or subsequent to the time of breast fluid expression. Suitable solid phase media in this context include microscopic glass slides, capillary tubes, coated tubes, microtiter wells or plates, membranes, filters, affinity columns, dot blot matrices, beads, resins, and other like media that will selectively adsorb, bind, filter, partition or otherwise process desired components of the mammary fluid for convenient incorporation into a desired assay.

A wide range of sample collection procedures and materials known in the art are useful within the invention.

Selected methods and materials will vary among different assays, as will be understood and readily practiced by those skilled in the art. For example, if the breast disease marker sought in a particular assay is a soluble protein, it will often be desired to immobilize the protein on a solid phase matrix or template by contacting the target protein with a reagent having high specificity for the protein, preferably a polyclonal or monoclonal antibody. The yields a complex, eg., a ligand-protein complex, an antibody-antigen complex, or other complex in which the target protein is bound to a specific binding partner (i.e., wherein the complex is not dissociated upon addition of a non-specific binding partner conventionally used as a control to determine specific binding; and preferably wherein the binding partner binds with an affinity of kD $10^{-9}$ or greater). The binding partner which binds to the target protein is in turn immobilized to the solid phase medium, before or after complex formation with the target protein. Immobilization of the binding partner, eg., by covalent binding to a solid phase template or matrix, can be achieved by a variety of conventional methods known in the art.

In this manner, the target protein/binding partner complex is adsorbed or otherwise bound directly to an insoluble matrix. Alternatively, a variety of secondary binding partners, eg., anti-isotype antibodies, may be added to bind the complex to the insoluble matrix. The latter step depends on the nature of the first binding partner (i.e., the binding agent that specifically binds the target protein), for example whether the first binding partner is a primary antibody, ligand, etc.

Particularly useful within the invention are immunoassay which formats employ a combination of solid phase or immobilized reagents and labeled reagents whereby the association of the label with the solid phase is a function of the presence or absence of reactivity with the targeted antigen. In general, such a solid phase reagent comprises a binding substance such as an anti-antibody (eg., anti-IgG), or other immunobinder or other binding agent according to the assay protocol involved, bound or attached, covalently or noncovalently, to the solid phase matrix or in an otherwise immobilized form.

Useful labeled reagents in solid phase immunoassays include a binding substance such as an anti-antibody (eg., anti-IgG), or other immunobinder or other binding agent according to the assay protocol involved, which is chemically coupled with a detectable chemical moiety. Useful labels are conventional in the art and include fluorescers, chemiluminescers, radioisotopes, and enzymes. Enzyme labels are particularly useful and are generally selected from alkaline phosphatase, peroxidase, and ©β-galactosidase.

Enzyme labels are readily detectable by addition of a corresponding chromogenic substrate and detecting the resulting color or fluorescent response.

A variation of this protocol uses a ligand-modified form of the targeted antigen(s) with immobilization to the solid phase being accomplished by using a solid phase bearing an immobilized (eg., bound or adsorbed) binding partner to the ligand. For example, biotin or a hapten (eg., fluorescein) can be used as the ligand and can be immobilized by contact with a solid phase form of avidin or anti-hapten antibody, respectively. The addition of the solid phase binding partner can occur at any convenient time in the assay, such as prior to contact of sample with the ligand-antigens(s) or thereafter.

Preferred solid phase matrices for use within the foregoing methods include *Staphylococcus aureus* or Protein A or G Agarose [eg. Sepharose® (Pharmacia Biotech AB, Uppsala, Sweden)] beads. Protein A and protein G are cell wall proteins isolated from specific bacterial strains, and have specific binding sites for certain classes of immunoglobulins. Protein A binds (to varying degrees) most subclasses of IgG, plus IgM, IgA, and IgD. Protein G binds nearly all subclasses of IgG, but not other classes of immunoglobulins.

An alternative solid phase sample collection and/or assay method utilizes a specific anti-marker primary antibody which is covalently attached to the solid phase matrix, eg., by covalent linking the antibody through its free amino groups to cyanogen-bromide-activated Sepharose particles. Insolubilized antibody can be used to pull the corresponding marker antigen out of solution by adsorption to its surface. In yet another alternative format, the marker protein can be treated with a cross-linking reagent (eg. biotin or digoxigenin) which may be subsequently detected by a second binding partner. In the case of biotin, the second binding partner is avidin or streptavidin; for digoxigenin, the second reagent is an anti-digoxigenin antibody. Avidin and streptavidin may be coupled directly to the solid phase medium, eg., to agarose beads. Because the initial biotinylation is not specific for the marker, samples are frequently electrophoresed on, eg., SDS PAGE, transferred to nitrocellulose etc., and Western blotted with antibodies specific for the protein factor.

A preferred assay method for detecting protein markers is the well known, Enzyme Linked Immunosorbant Assay (ELISA) assay. According to this method, a variety of coating reagents can be adsorbed or otherwise bound directly onto a surface of a desired solid phase sample collection medium, eg., a microtiter plate, well, tube, bead, test strip, plastic microparticle, latex particle, etc., to form a coated template or matrix. These coating reagents are typically a species specific anti-isotype antibody (eg., anti-mouse-IgG) but can also include an anti-marker primary antibody or an affinity reagent such as avidin or streptavidin. The target protein (eg., a soluble protein marker) is contacted with a specific primary antibody or, alternatively, is crosslinked (eg., to biotin) or otherwise modified to form a complex, and the resulting complex is adsorbed to the coated template or matrix and processed according to conventional assay methods.

Latex or particle agglutination methods are also to be mentioned. Particles are coated or covalently coupled with a target antigen, ligand, antibody or other binding partner. The particles are then incubated with a test sample and resulting agglutination of the particles, eg., due to formation of ICA antibody linkages between particles, is detected. Detection can be accomplished by visual observation (eg., a slide agglutination format) or quantified by measuring turbidity changes with a spectrophotometer or nephelometer. A well known variation of this general method based on inhibition of particle agglutination can also be employed. In addition, an agglutinator reagent can be prepared comprising multiple antigens, eg., a water soluble polymer backbone to which are attached multiples of one or more antigens within a panel.

Alternative methods for collecting and analyzing samples within the invention include Western immunoblot and dot-blot methods. For application of these methods, the solid phase sample collection medium is preferably a membrane or filter, eg., a nitrocellulose, polyvinylidene difluoride (PVDF), or nylon membrane. Proteins within the breast fluid sample may be processed (eg., separated on SDS PAGE) or directly transferred to the membrane, and non-specific interactions may be blocked by incubating the membrane with, eg., bovine serum albumin/ovalbumin or non-fat dry milk. A primary antibody with specificity for the protein marker is contacted with the membrane, and excess antibody is washed, eg., with buffered detergent. A labelled isotype specific antibody is next contacted with the membrane, and target protein-primary antibody-secondary antibody ternary complexes are detected, eg., calorimetrically.

Where the targeted protein factor includes a carbohydrate moiety, the factor can also be adsorbed to a solid phase template or matrix, eg., a resin, by way of lectin-carbohydrate interactions. Various lectins are available for this purpose which differ in their carbohydrate binding specificity. For example, Lectin Con A binds to mannose-containing carbohydrate structures and with low affinity to α-glucose and α-N-acetylglucosamine. Lectin GNA binds to terminal mannose residues. Lectin MAA binds to α(2–3) Linked sialic acids. A variety of other lectins collectively providing a wide range of specificities are known in the art.

A particularly preferred solid phase sample collection medium for use within the invention is a filter, pad or membrane that can be directly contacted to a sample of expressed breast fluid to adsorb, absorb, bind, partition or otherwise facilitate sample processing or handling within a selected assay. For this purpose, several types of transfer membranes are known, including nitrocellulose which is the most commonly used transfer membrane. Several commercial sources now offer nitrocellulose impregnated with a synthetic support which improves its durability and flexibility without altering its performance. One preferred transfer membrane, polyvinylidene difluoride (PVDF), marketed by Millipore (Bedford, Mass.) under the trade name IMMOBILON®, has slightly lower protein-binding capacity than nitrocellulose but is mechanically stronger and compatible with many organic solvents. This allows direct protein staining with Coomassie Blue, and direct amino acid composition and sequence analysis of transferred proteins, without interfering with its subsequent use for antibody probing.

Membranes are not only useful within the invention for protein blotting, but also for immobilization of nucleic acids. Thus, nitrocellulose, reinforced nitrocellulose, diazotized membranes (paper or nylon), nylon, charged nylon, or PVDF, and DEAE-anion exchange membranes are useful for immobilizing DNA and RNA from expressed breast fluid. In this context, the most commonly used membranes are reinforced nitrocellulose and nylon. Nitrocellulose has a lower background but also a lower binding capacity than nylon and is chosen primarily when background, but not detectability, is the main concern. Nylon, in contrast, is ideal for lower copy number sequences, short target sequences (down to oligomers) or for reprobing. Membranes are also available with different pore sizes. For DNA blots, membranes with a pore size of 0.45 μm are usually chosen for large fragments, but 0.22 μm for fragments of <500 bases. For RNA blots, membranes with a pore size of 0.1 or 0.22 μm are most efficient. Membranes are available in different size specifications, including sheets, rolls, pre-cut circles, etc.

Methods for detecting DNA on nylon without DNA purification and processing of the samples, eg., for detecting DNA from fluids or whole cells, have recently been developed (Reed and Matthaei, Nucleic Acids Res. 18: 3093 (1990; Hammermueller et al., J. Virol. Methods 31: 47 (1991), each incorporated herein by reference). These procedures avoid enzymatic dispersion of cells, RNase and pronase treatments to hydrolyze cellular macro-molecules, etc., and are typically based on the capacity of alkali and other reagents to disperse and solubilize cells and hydrolyze macro-molecules including RNA and protein, but not DNA. Positively charged modified nylon membranes then irreversibly bind nucleic acid while remaining suitable for hybridization.

Nucleic acid extraction and processing steps may also be minimized by well known fast blot methods. In particular, fast blot methods which use nylon as a solid phase take advantage of the ability of NaOH to dissociate cells, denature DNA and immobilize DNA. Nitrocellulose membranes have a lower binding capacity and co-immobilization of nucleic acid and protein from neutral solutions can be a problem. Concentrated NaI can be used to inhibit protein immobilization, to denature DNA and to irreversibly bind the nucleic acid to nitrocellulose without a requirement for baking. This method can also be used for RNA.

Although it is possible to directly transfer proteins, nucleic acids and other markers to a solid phase matrix which is in turn directly incorporated in an assay, it may be desirable to concentrate the target marker, eg., by chromatography, extraction, specific or nonspecific adsorption, etc., particularly when sensitivity is a problem. Thus, samples can be collected and initially processed by contacting breast fluid with a solid phase chromatographic medium, eg., within a cartridge comprising a micro-column of Sepharose-coupled antibody. Up to 500-fold increases in immunoassay sensitivity with apparent recoveries of 85 to 95% can be achieved using this approach. This and other well known chromatographic procedures provide a powerful approach to the quantitation of substances too dilute to be measured by routine methods.

For sample collection and processing using chromatographic and related methods, a particulate solid phase sample collection medium is preferred. Various particulate media are known which selectively adsorb, absorb, bind, or partition components of biological samples, which media are readily adapted for collection and processing of breast fluid samples. These particulate can be coupled with various coating reagents known in the art, eg., affinity reagents, to provided a coated medium, or may be used in an unmodified form.

Exemplary particulate sample collection media for use within the invention include beads, plastic microparticles, latex microspheres, glass materials such as controlled porous glass, granular agarose based materials, cross-linked dextran polymers, inorganic or organic ion exchanger materials, kieselsur and other silicate materials. Suitable materials additionally include cellulosic materials, eg., diethylaminoethyl (DEAE) cellulose or diethylamino (DEA) cellulose. Also useful are natural polymeric carbohydrates and their synthetically modified, cross-linked or substituted derivatives, such as agar, agarose and cross-linked dextran polymers.

Synthetic polymers which can be prepared with suitably porous structures, such as vinyl polymers (eg., polyethylene, polypropylene, polystyrene, polyvinylchloride, polyvinylacetate and its partially hydrolysed derivatives, polyacrylates, polyacrylamides, polymethacrylates), copolymers and terpolymers of the above vinyl monomers among themselves and with other monomers, polycondensates (eg., polyesters and polyamides), and addition polymers, such as polyurethanes or polyepoxides are also useful.

Yet additional particulate media are prepared from inorganic materials having a suitably porous form, such as sulfates or carbonates of alkaline earth metals and magnesium. Examples include barium sulfate, calcium sulfate, calcium carbonate, magnesium carbonate, silicates of alkali and alkaline earth metals and/or aluminum and/or magnesium, and aluminum or silicon oxides or hydrates, such as clays, alumina, talc, kaolin, zeolite, among others.

Also included among useful solid phase sample collection media porous barrier materials suitable for use with breast pump and breast pump adapter devices of the invention, for example to enclose particulate solid phase media within a cartridge adapted for coupling in fluid connection with a breast pump or breast pump adapter. Such porous barrier materials are inert to and nonreactive with markers and other analytes and reagents used in assaying for breast disease markers, and are porous with respect to the passage of liquids and/or particulates of a pre-selected size. Suitable materials include various porous materials such as nylon fabric, polyethylene and other plastic films, membranes, filters, glass wool, sponge, styrofoam, ceramic and other porous materials.

In conjunction with sample collection, samples of expressed breast fluid may be exposed to other agents such as buffers, diluents, extraction or chromatographic media, cross-linking agents, blocking agents, denaturing agents, etc., to stabilize or otherwise prepare the sample for processing within a desired assay. For example, the sample may be diluted (eg., by collecting the sample in a well or recess containing the solid phase medium wetted or suspended in a diluent) to minimize nonspecific binding effects, eg., affecting a subsequent immunoassay. In the exemplary context of sample collection for immunoassays, the avidity of the antibody for the marker antigen is an important consideration, whereby providing more or less diluent during sample collection and incubation may optimize a particular antigen-antibody system being studied.

Commonly used buffers for dilution include phosphate, borate, or Tris-buffered saline. Usually, the choice of the buffer is not important. Nonetheless, a careful examination of the effect of buffer, pH, ionic strength, and divalent cations will facilitate use of a new sample collection/assay system in order to maximize sensitivity and resolve possible sources of interference within the assay. Although immunoassays are usually carried out at neutrality, doing so is not always optimal.

Nonspecific binding or adsorption, eg., of antigens and haptens (especially hydrophobic haptens) to glass and plastic tubes or pipets may markedly influence measured activity in a particular immunoassay. With some proteins and polypeptides, nonspecific binding in immunoassays is reduced if plastic tubes are used. The addition of protein to the medium may also minimize nonspecific adsorption and help avoid denaturation of highly diluted antigens and antibodies. Therefore, assays involving iodinated antigens are generally carried out in protein-containing buffers. Bovine serum albumin, gelatin, lysozyme, and ovalbumin are commonly used, usually at final concentrations of 1 to 5 mg/ml. In some systems diluted whole serum or proteins present in the sample itself are just as satisfactory. However, even though added proteins are often beneficial, they should not be used indiscriminately without making an evaluation for possible adverse effects, for example contaminating enzymes that may degrade the marker protein.

Other possible additives for improved sample collection and assay methods, apart from buffer and protein, include enzyme inhibitors and chelating agents. In assays lasting longer than 3 days, a bacteriostatic agent, such as sodium azide, 0.1 to 0.2%, may also be incorporated into the sample collection and/or assay medium to help avoid microbial growth.

Although a fundamental utility of the present invention lies in the novel, non-invasive methods for obtaining biological samples from mammary fluid, additional methods are disclosed herein that provide useful assays for detecting and/or measuring important breast disease markers in these samples. In this context, the invention provides a broad range of assay methods incorporating known procedures and reagents for determining the presence and/or expression levels of breast disease markers, particularly breast cancer markers, in biological samples. As incorporated within the invention, these methods involve administration of oxytocin to mammalian patients, preferably via intranasal administration, in amounts effective to stimulate mammary fluid expression in the patient, as described above. Once a sufficient post-administration time period has elapsed to allow the oxytocin to reach and stimulate target alveolar-ductal tissues, the breast is pumped and a biological sample is collected, as described above. After the sample is collected, a bioassay is conducted on the sample to determine the presence and/or amount of a selected breast disease marker, preferably a breast cancer marker or panel of breast cancer markers, in the sample.

As used herein, the term breast disease marker refers to any cell, cell fragment, protein, peptide, glycoprotein, lipid, glycolipid, proteolipid, or other molecular or biological material that is uniquely expressed (eg. as a cell surface or secreted protein) by diseased breast cells, or is expressed at a statistically significant, measurably increased or decreased level by diseased breast cells, or in association with breast disease (eg. a protein expressed by an infectious agent associated with breast disease), or is expressed at a statistically significant, measurably increased or decreased level by diseased breast cells compared to normal breast cells, or which is expressed by non-diseased breast cells in association with breast disease (eg. in response to the presence of diseased breast cells or substances produced therefrom). Breast disease markers can also include specific DNA or RNA sequences marking a deleterious genetic change, or an alteration in patterns or levels of gene expression significantly associated with breast disease. Preferred breast disease markers include markers of breast infections, benign neoplasia, malignant neoplasia, pre-cancerous conditions, and conditions associated with an increased risk of cancer.

As used herein, the term breast cancer marker refers to a subset of breast disease markers, namely any protein, peptide, glycoprotein, lipid, glycolipid, proteolipid, or other molecular or biological material that is uniquely expressed (eg. as a cell surface or secreted protein) by cancerous cells, or is expressed at a statistically significant, measurably increased or decreased level by cancerous cells compared to normal cells, or which is expressed by non-cancerous cells in association with cancer (eg. in response to the presence of cancerous cells or substances produced therefrom). Breast cancer markers can also include specific DNA or RNA sequences marking a deleterious genetic change, or an alteration in patterns or levels of gene expression significantly associated with cancer. In addition, breast cancer markers can include cytological features of whole cells present in mammary fluid, such as nuclear inclusions or cytoplasmic structures or staining attributes uniquely expressed by, or associated with, cancerous cells.

Among the breast cancer markers that are useful within the methods of the invention, a subset are described in representative review articles by Porter-Jordan et al., *Hematol. Oncol. Clin. North Amer.* 8: 73–100, 1994; and Greiner, *Pharmaceutical Tech*, May, 1993, pp. 28–44, each incorporated herein by reference in its entirety. Other suitable markers are also widely known and can be readily incorporated into the methods of the invention using information and methods generally known or available in the literature. Preferred breast cancer markers for use within the invention include well characterized markers that have been shown to have important value for determining prognostic and/or treatment-related variables in human female patients. As noted previously, prognostic variables are those variables that serve to predict outcome of disease, such as the likelihood or timing of relapse or survival. Treatment-related variables predict the likelihood of success or failure of a given therapeutic program. Determining the presence or level of expression or activity of one or more of these markers can aid in the differential diagnosis of patients with malignant and benign abnormalities, and can be useful for predicting the risk of future relapse or the likelihood of response to a selected therapeutic option.

It is important to note, however, that the invention does not rely solely on breast disease markers that meet the stringent requirements of sensitivity and specificity that would render the marker immediately acceptable for clinical application to human patients. On the contrary, a number of breast disease markers contemplated within the invention fall short of these stringent criteria, and nonetheless provide useful information that can be of substantial benefit in detecting, differentially diagnosing or managing breast cancer. Such non-clinically accepted markers are useful for immediate application within the methods of the invention as basic research tools, and as adjunctive tools in clinical applications. Beyond these immediate applications, many such markers are expected to be further developed and refined according to the methods of the invention to the point of direct clinical applicability, particularly in assay methods that analyze combinations of markers to generate complementary data of greater predictive value than data yielded by individual markers alone.

The preferred assay methods of the invention particularly focus on breast cancer markers associated with tumorigenesis, tumor growth, neovascularization and cancer invasion, and which by virtue of this association provide important information concerning the risk, presence, status or future behavior of cancer in a patient. As noted previously, tumorigenesis and tumor growth can be assessed using a variety of cell proliferation markers (for example Ki67, cyclin D1 and PCNA). Tumor growth can also be evaluated using a variety of growth factor and hormone markers (for example estrogen, EGF, erbB-2, and TGF-U, receptors of autocrine or exocrine growth factors and hormones (for example IGF and EGF receptors), or angiogenic factors. In addition to tumorigenic, proliferation and growth markers, a number of markers provide information concerning cancer invasion or metastatic potential in cancer cells, for example by indicating changes in the expression or activity of cell adhesion or motility factors. Exemplary markers in this context include Cathepsin D, plasminogen activators and collagenases. In addition, expression levels of several putative tumor "suppressor" genes, including nm23, p53 and rb, provide important data concerning metastatic potential, or growth regulation of cancer cells. A large number and variety of suitable breast cancer markers in each of these classes have been identified, and many of these have been shown to have important value for determining prognostic and/or treatment-related variables relating to breast cancer.

Prior to or concurrent with each assay run of the invention, it may be preferable to perform a preliminary evaluation to verify sample origin and/or quality. The focus of such preliminary evaluations is to verify that the sample collected from expressed mammary fluid is indeed of mammary origin, and is not contaminated with other potential contaminants, such as sweat from skin surrounding the nipple. For these sample verification purposes, a variety of assays are available which identify mammary fluid markers known to be present in mammalian mammary fluid, and which are preferably highly specific markers for mammary fluid (i.e. markers which are typically always present in mammary fluid and which are absent from all, or most of, other potentially contaminating bodily fluids and tissues). However, an acceptable level of specificity for mammary fluid markers within the methods of the invention is provided by markers that are simply known to be present in mammary fluid, even though they may be present in other bodily fluids. One such marker is the enzyme lysozyme, which is a normal component of human serum, urine, saliva, tears, nasal secretions, vaginal secretions, seminal fluid, and mammary fluid. Lysozyme (muramidase) is an enzyme which hydrolyzes beta 1,4-glycosidic linkages in the mucopolysaccharide cell wall of a variety of microorganisms resulting in cell lysis. Quantitative measurement of lysozyme is readily accomplished by a well known agar plate diffusion method, described in detail in the instructions provided with the QUANTIPLATE® lysozyme test kit, available from Kallestad, Sanofi Diagnostics (Chasta, Minn.), incorporated herein by reference in its entirety.

Other mammary fluid markers for sample verification that are more specific than lysozyme are preferred within the methods of the invention, and can be readily incorporated within the invention based on published and generally known information. The most preferred among these markers are proteins and other biological substances that are specifically expressed or enriched in mammary fluid. A diverse array of suitable markers in this context have been characterized and have already been used to develop specific antibodies, including affinity purified and monoclonal antibodies. These antibodies can in turn be employed as immunological probes to determine the presence or absence, and/or to quantify, selected mammary fluid markers to verify mammary fluid sample origin and quality. Mammary fluid markers of particular interest for use within the invention include specific cytokeratins that are characteristically expressed by normal and cancerous mammary epithelial cells, against which specific panels of antibody probes have already been developed. (See for example, Nagle, *J. Histochem. Cytochem.* 34: 869–881, 1986, incorporated herein by reference in its entirety). Also useful as mammary fluid markers are the human mammary epithelial antigens (HME-Ags) corresponding to glycoprotein components of the human milk fat globulin (HMFG) protein, against which specific antibodies (eg., anti HMFG1, Unipath, U.K.) are also available. (See Rosner et al., *Cancer Invest.* 13: 573–582, 1995; Ceriani et al. *Proc. Natl. Acad. Sci. USA* 74: 582–586, 1982; Ceriani et al., *Breast Cancer Res. Treat.* 15; 161–174, 1990, each incorporated herein by reference in D its entirety).

To conduct the breast disease marker assays provided within the invention, a collected biological sample from mammary fluid is generally exposed to a probe that specifically binds to a selected breast disease or breast 3 cancer marker, or otherwise interacts with the marker in a detectable manner to indicate the presence or absence, or amount, of the breast disease or breast cancer marker in the sample. Selected probes for this purpose will generally depend on the characteristics of the breast disease marker, i.e. on whether the marker is a protein polynucleotide or other substance. In preferred embodiments of the invention, the breast disease marker is a protein, peptide or glycoprotein, all of which are effectively targeted in breast disease marker assays using specific immunological probes. These immunological probes can be labeled with a covalently bound label to provide a signal for detecting the probe, or can be indirectly labeled, for example by a labeled secondary antibody that binds the immunological probe to provide a detectable signal.

General methods for the production of non-human antisera or monoclonal antibodies (eg., murine, lagormorpha, porcine, equine) are well known and may be accomplished by, for example, immunizing an animal with a selected breast disease marker protein, peptides synthesized to include part of the marker protein sequence, degradation products including part of the marker protein sequence, or fusion proteins including all or part of the marker protein linked to a heterologous protein or peptide. Within various embodiments, monoclonal antibody producing cells are obtained from immunized animals, immortalized and screened, or screened first for the production of an antibody that binds to the selected breast cancer marker protein or peptide, and then immortalized. It may be desirable to transfer the antigen binding regions (i.e., F(ab')2 or hypervariable regions) of non-human antibodies into the framework of a human antibody by recombinant DNA techniques to produce a substantially human molecule. Methods for producing such "humanized" molecules are generally well known and described in, for example, U.S. Pat. No. 4,816, 397 (incorporated herein by reference in its entirety). Alternatively, a human monoclonal antibody or portions thereof may be identified by first screening a human B-cell cDNA library for DNA molecules that encode antibodies that specifically bind to the selected breast disease marker according to the method generally set forth by Huse et al. (*Science* 246: 1275–1281, 1989 (incorporated herein by reference in its entirety). The DNA molecule may then be cloned and amplified to obtain sequences that encode the antibody (or binding domain) of the desired specificity.

Also contemplated within the invention are bifunctional antibodies having independent antigen binding sites on each immunoglobulin molecule (as disclosed for example in *Thromb. Res. Suppl. X:* 83, 1990, and in *The Second Annual IBC International Conference on Antibody Engineering*, A. George ed., Dec. 16–18, 1991; each incorporated herein by reference in its entirety), as well as panels of individual antibodies having differing specificities. Bifunctional antibodies and antibody panels of particular use within the invention include antibodies and panels of antibodies that bind to two or more selected breast disease markers to generate complementary data of greater predictive value than data yielded by individual markers alone.

Monoclonal antibodies are particularly useful within the invention as labeled probes to detect, image and/or quantify the presence or activity of selected breast disease markers. In this context, monoclonal antibodies that specifically bind to selected breast disease markers are provided which incorporate one or more well known labels, such as a dye, fluorescent tag or radiolabel. By incorporating such a label, the antibodies can be employed in routine assays to determine expression, localization and/or activity of one or more selected breast disease markers in a biological sample including, or derived from, mammary fluid. Results of these assays to determine expression, localization and/or activity of a selected breast disease marker in a test sample taken from a patient at risk for breast disease, or known to have breast disease, can be compared to results from control studies detecting and/or quantifying the same marker in biological samples obtained from normal patients negative for breast disease. In this manner, baseline data and cutoff values can be determined according to routine methods to refine the assays of the invention and adapt them for direct clinical application.

Detection and/or quantification of breast disease markers in the biological samples of the invention can be accomplished using a variety of methods. Preferred methods in this regard include well known ELISA immunoassays, immunoprecipitation assays, and various solid phase immunoassays including Western blotting, dot blotting and affinity purification immunoassays, among other methods. Comparable methods are disclosed herein, or are elsewhere disclosed and known in the art, for using non-antibody probes to detect and/or quantify the expression and/or activity of breast disease markers. Suitable non-antibody probes for use within the invention include, for example, labeled nucleotide probes that hybridize at moderate or high stringency to DNA transcripts of oncogenes and other DNA sequences associated with elevated breast disease risk, or with mRNA transcripts encoding breast disease marker proteins. Preferably, the nucleotide probes hybridize with a target sequence under high stringency conditions. As used herein, "moderate stringency" and high stringency" refers to finite ranges of hybridization conditions that are well established in the literature. (See, for example: Sambrook et al., (1989) *Molecular Cloning A Laboratory Manual* (Cold Spring Harbor, N.Y.: Cold Spring Harbor Press); Hames and Higgins, eds., *Nucleic Acid Hybridization A Practical Approach*, IRL Press, Washington D.C., 1985; Berger and Kimmel, eds, *Methods in Enzymology, Vol. 52, Guide to Molecular Cloning Techniques*, Academic Press Inc., New York, NY, 1987; and Bothwell, Yancopoulos and Alt, eds, *Methods for Cloning and Analysis of Eukaryotic Genes*, Jones and Bartlett Publishers, Boston, MA 1990; each of which is incorporated herein by reference in its entirety. Moderate or high stringency hybridization conditions are achieved, eg., by adjusting the temperature of hybridization, adjusting the percentage of helix-destabilizing agents such as formamide in the hybridization mix, and adjusting the temperature and salt concentration of the wash solutions. Alternatively, stringency can be adjusted during post-hybridization washes by varying the salt concentration and/or the temperature. Stringency of hybridization may be reduced by reducing the percentage of formamide in the hybridization solution or by decreasing the temperature of the wash solution. Typical high stringency conditions require, for example, high temperature hybridization (eg., 65–68° C. in aqueous solution containing 4–6×SSC, or 42° C. in 50% formamide) combined with a high temperature (eg., 5–25° C. below the To) wash and a low salt concentration (eg., 0.1×SSC). In contrast, moderate stringency conditions involve, for example, hybridization at a temperature between 50° C. and 55° C. and washes in 0.1×SSC, 0.1% SDS at between 50° C. and 55° C., which should be sufficient to identify polynucleotide molecules encoding I-mf from other species or to isolate isoforms of I-mf. In further contrast, low stringency conditions involve, for example, low hybridization temperatures (eg., 35–42° C. in 20–50% formamide) and intermediate temperature (eg., 40–60° C.) washes in a higher salt concentration (eg., 2–6×SSC).

In certain preferred embodiments of the invention, cDNA and oligonucleotide probes are employed in well known Northern, Southern and dot-blot assays for identifying and quantifying the level of expression of a selected breast disease marker in cell samples collected from expressed mammary fluid.

Other suitable probes for use within the invention include labeled ligands, binding partners and co-factors of breast disease markers (eg. growth factor receptor ligands, or substrates of breast cancer associated proteases such as cathepsin D).

Measuring the level of expression of breast disease markers according to the foregoing methods will provide important prognostic and treatment-related information for assessing a broad range of breast disease, including the genesis, growth and invasiveness of cancer, in mammals, particularly humans. For example, assays utilizing oligonucleotide probes will assist early screening to evaluate heritable genetic lesions associated with breast cancer, and to distinguish between pre-cancerous, early cancerous and likely metastatic lesions in patients.

In addition to the above mentioned sample collection and assay methods, the invention also provides kits and multi-container units comprising reagents and components for practicing the sample collection and assay methods of the invention. Briefly, these kits include basic components for obtaining a biological sample from mammary fluid, including a pharmaceutical preparation of oxytocin in a biologically suitable carrier. Preferably, the oxytocin preparation is provided in an intranasal spray applicator and contains approximately 40 USP units of oxytocin per ml of liquid carrier, which carrier is a simple, inexpensive buffered saline solution. Preferred applicators can be in any of a variety of pressurized aerosol or hand-pump reservoir forms, with a nozzle for directing a liquid spray of the oxytocin into a patient's nostril. The kits also preferably include a collecting device for collecting a biological sample from the expressed mammary fluid, which collecting device may range from a simple fluid reservoir to solid phase media that can be directly incorporated into solid phase bioassays. In this context, an optional breast pump may also be provided that is applicable to a human breast and designed to generate intermittent or sustained negative pressures in an area surrounding the nipple of between about 50–200 mm Hg. More preferably, the breast pump serves a dual purpose of applying negative pressure to the breast to facilitate mammary fluid expression from the nipple following oxytocin stimulation, and to provide a reservoir or solid phase collecting device incorporated within the breast pump for biological sample collection.

Kits for practicing the assay methods of the invention include a suitable container or other device for collecting a biological sample from expressed mammary fluid. A range of suitable collection devices are contemplated corresponding to a wide range of suitable biological samples that may be collected from the expressed mammary fluid. For example, simple sterile containers or reservoirs are provided to collect whole mammary fluid. Alternatively, a variety of solid phase devices, including microscopic glass slides, membranes, filters, beads and like media, are provided to receive or partition selected liquid or solid fractions of the mammary fluid, to receive or partition cells or cellular constituents from the mammary fluid, or to receive or partition purified or bulk proteins, glycoproteins, peptides, nucleotides (including DNA and RNA polynucleotides) or other like biochemical and molecular constituents from the mammary fluid. A wide variety of such sample collection devices are disclosed herein, or are otherwise widely known or described in the literature, which can be readily adapted for use within specific embodiments of the invention. These collection devices may be provided as a component of the breast pump (such as a removable nitrocellulose filter placed within the pump to directly receive or contact the expressed mammary fluid as it is pumped), or may be provided separately (for example as a non-integral membrane, filter, affinity column or blotting material to which mammary fluid or mammary fluid components are exposed to collect a biological sample for assay purposes).

In more detailed embodiments of the invention, kits include reagents and/or devices for detecting the presence and/or amount of a breast disease marker in the biological sample, for example an immunological or molecular probe that binds or reacts with a breast cancer marker. Among these possible reagents or devices are immunological and non-immunological probes for detecting the presence or amount of a breast cancer marker in the biological sample. The kits may also contain suitable buffers, preservatives such as protease inhibitors, direct or sandwich-type labels for labeling the probes, and/or developing reagents for detecting a signal from the label. In one aspect, kits of the present invention contain monoclonal antibodies useful for detecting and/or measuring a breast cancer marker in a sample. Such antibodies may be pre-labeled, or may be detected by binding to a secondary antibody optionally included in the kit. The antibody reagents may be provided in a separate container, or may be provided in combination in a series of containers. Within yet another aspect of the invention, kits contain sequence-specific oligonucleotide primers for detecting polynucleotide molecules encoding breast cancer marker proteins. Such primers may be provided in separate containers, or may be provided in combinations of one or more primer pairs in a series of containers. A broad selection of other kits are provided within the invention based on general knowledge in the art and on the description herein, including kits that contain specific instructions for carrying out the assays of the invention.

Also provided within the invention are methods for obtaining a biological sample from a patient and/or determining the amount of a breast disease marker in a biological sample from breast fluid, which methods employ a novel breast pump 10 or breast pump adapter 12, as described hereinbelow. These methods include a step of applying the breast pump to assist breast fluid expression, wherein a solid phase sample collection medium is fluidly connected with the breast pump. The solid phase sample collection medium may be integrated within the breast pump or otherwise fluidly connected with the pump, so that an expressed breast fluid sample contacts the collection medium while the pump remains applied to the breast.

To practice these aspects of the invention, the breast pump 10 (FIG. 1) and breast pump adapter 12 (FIG. 11) each have fluidly connected therewith a solid phase sample collection medium selected from any of the solid phase media described hereinabove. The breast pump may be generally constructed according to various conventional breast pump designs, for example according to the general design described in U.S. Pat. No. 4,929,229 and U.S. Pat. No. 5,007,899 to Larsson; U.S. Pat. No. 5,601,531 to Silver; U.S. Pat. No. 3,786,801 to Sartorius; or U.S. Pat. No. 5,295,957 to Aida et al.

As with other conventional breast pumps, the breast pump of the invention includes a breast engaging portion 14 constructed of a non-porous material. The engaging portion is sized and dimensioned to receive at least a nipple 16 portion of a breast 17 and form a suction seal therewith. Preferably, the breast engaging portion is sized and dimensioned to receive at least an areolar portion of the breast, and more preferably a distal quarter to one-half or larger portion of the breast (eg., as shown in FIG. 1), and form a suction seal therewith. Different sizes and dimension of the breast engaging member may be selected, eg., to receive human breasts of differing sizes. Alternatively, devices for veterinary use are provided wherein the breast engaging member is sized and dimensioned to receive a breast of a non-human mammal.

To form a suction seal with the breast 17 as described above, the breast engaging portion 14 of the pump 10 may be constructed in a variety of shapes and dimensions. In one embodiment the engaging portion is formed as a simple cylinder, tube or funnel shaped and dimensioned to engage the nipple 16 or areolar portion of the breast in a suction seal. Preferably, a terminal edge 18 of the engaging portion is rounded or flared so that the edge does not impinge uncomfortably against the skin of breast 17 when negative pressure is applied to the breast to form the suction seal. In preferred embodiments the engaging portion is roughly funnel shaped to comfortably engage a distal quarter to one half or larger portion of the breast, as shown in FIG. 1 and form a suction seal therewith.

The breast engaging portion 14 of the breast pump 10 can be constructed of any suitable non-porous material which is inert to body fluids and which has sufficient rigidity to prevent collapse of the engaging portion when negative pressure is applied against its inner walls 20. Preferably, the engaging portion and other parts of the breast pump are autoclavable for sterilization purposes. Thus, the engaging portion may be constructed of a rigid material such as a polypropylene, polyurethane, polyvinyl plastic, polymethyl methacrylate, and the like. Alternatively, the engaging portion may be constructed of a semi-rigid material which prevents collapse but allows for manual compression of at least a base 22 of the engaging portion to massage the nipple 16 and/or areolar region of the breast 17 to facilitate breast fluid expression. Suitable materials in this context include rubber or synthetic elastomers, eg., silicon plastic (silastic) and like materials. Preferably, the material which forms the engaging portion is transparent to allow a physician or technician using the breast pump to visualize the breast 17 to determine its positioning and condition during application of the pump and to observe fluid expression from the nipple.

The breast engaging portion 14 of the breast pump 10 is fluidly connected to a sample collection housing 30 made of a rigid material (preferably transparent plastic) which supports a solid phase sample collection medium in fluid connection with the engaging portion. In one aspect of the invention the housing supports a pad, or sheet, 38 of absorbent or adsorbent material, for example a membrane 39 or filter 40 pad or sheet (FIGS. 2–5). Multiple pads or sheets (of the same or different material) may be used in combination. For example, a membrane 39 (eg., nitrocellulose) may be supported on a filter 40 (eg., a paper filter) as shown in FIG. 5. In this manner, a first sheet may serve as a support member, a wetting member, a wicking member, or a partitioning member for a second sheet, or may introduce or remove a chemical reagent, probe, blocking agent, buffering agent, denaturing agent, etc. therefrom. In one aspect, the multiple sheet materials partition components of the breast fluid (eg., by using different materials to retain different components of the breast fluid), thereby allowing for collection of different samples simultaneously.

Figure 9:
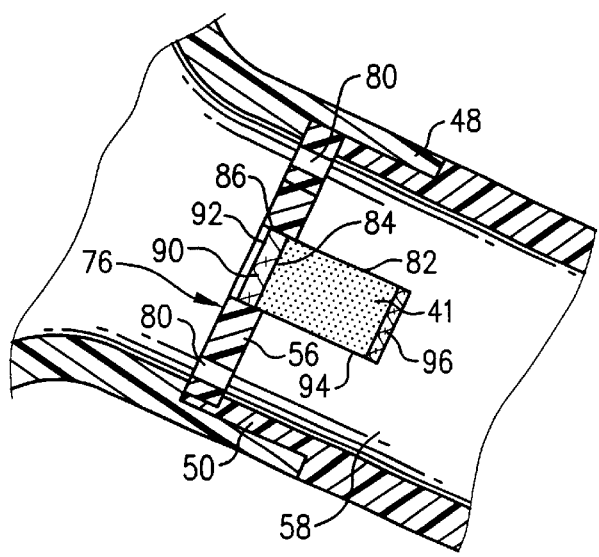
FIG. 9 is a sectional view of a portion of a breast pump illustrating a support member and cartridge for containing a particulate solid phase sample collection medium.

In another aspect of the invention the housing supports a particulate solid phase sample collection medium 41, for example beads, resins, microspheres, particulate chromatographic media (eg., agarose or silicate media), and the like (see, eg., FIG. 9). In yet another aspect of the invention, the housing supports a non-particulate solid template for sample collection, for example one or more capillary tubes 42 (FIG. 6), coated tubes 43 (FIG. 10), plates, wells, slides and the like formed of glass, plastic or other suitable materials.

Figure 10:
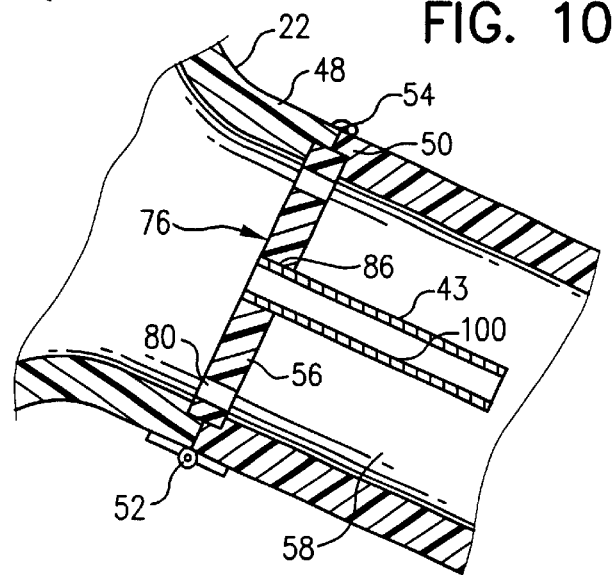
FIG. 10 is a sectional view of a portion of a breast pump illustrating a support member and an exemplary solid phase sample collection template (coated tube).

As shown in FIGS. 1 and 2, a preferred design of the breast pump 10 includes a removable coupling mechanism between the engaging portion 14 and the sample collection housing 30. A preferred coupling mechanism includes complementary threads 44, 46, disposed at mated connecting ends 48, 50 of the engaging portion, and housing, respectively. Alternatively, a simple pressure fit coupling may be provided to removably couple mated connecting ends 48, 50 of the engaging portion and housing, as shown in FIG. 9. In yet another alternative embodiment, the connecting ends 48, 50 are removably coupled by a hinge 52 and latch 54 that pivotally connects the two connecting ends (FIG. 10).

The sample collection housing 30 can support the solid phase sample collection medium in several ways, as exemplified in the drawings and also using a variety of equivalent designs that will be apparent to the artisan. In preferred embodiments of the invention, the solid phase medium is held on or within a support member 56 adapted to be fixedly interposed between the engaging portion 14 of the breast pump 10 and the housing.

Thus, in one exemplary design shown in FIGS. 1 and 2, the support member 56 is a removable disc spanning a lumen 58 of the housing and interposed between connecting ends 48, 50 of the engaging portion and housing. For use in conjunction with a variety of breast pump designs, a diameter 59 (FIG. 3) of the support member is between about ¼–3.0 inches, preferably about ½–2.0 inches, and more preferably about ¾–1 inches. In preferred aspects, the disc-shaped support member seats within a circumferential groove 60 in the connecting end 48 of the housing. A complementary circumferential groove 62 in the connecting end 46 of the engaging portion opposes the circumferential groove in the connecting end of the housing to sandwich the disc-shaped support member therebetween.

Prior to connecting the engaging portion 14 of the breast pump 30 with the housing 30, the support member is seated therebetween (eg. by fitting the support member within the opposing circumferential grooves 60, 62 of the housing and engaging portion). The force of connection (i.e. threading, pivoting or pushing the engaging portion and housing relative to one another) firmly sandwiches the support member in position between the engaging portion and housing.

To facilitate this purpose, the thickness (i.e., sectional height) 63 of the support member 56 is equal to or slightly greater than the height of a sidewall 64 of the circumferential groove 60 of the housing 30, whereby the support member is held in a friction fit and may be partially compressed when the engaging portion and housing are connected. Thus, the thickness of the support member is between about 2 mm to 5 cm, preferably about 3 mm to 2 cm, and more preferably about 4 mm to 1 cm. Consistent with this design, the support member can be made of a hard plastic material (eg., a hard polyvinyl or polyurethane), but is preferably made of a resilient, moderately compressible material, eg., soft plastic, rubber, or a waterproof fiber or composite material as used in conventional plumbing and automotive gaskets.

A disc-shaped support member 56 is well suited to support a sheet 38 of absorbent or adsorbent material, such as a membrane or filter. As shown in FIGS. 2 and 7, the sheet is preferably sandwiched between an upper retainer ring 66 and a lower retainer ring 68 of the support member to hold the sheet in place against negative pressure that may pass through the filter when a vacuum is applied through the engaging portion 14 and housing 30 (see below), as well as when the nipple 16 impinges against the sheet. The upper and lower retainer rings may be integrally joined in a disposable refill as shown in FIG. 2, or the two retainer rings may be separable to provide a reusable cassette for removing and inserting replacement sheets. An example of the latter design is depicted in FIG. 7, where the upper and lower retainer rings are releasably interconnected, eg., by a hinge 71 or other connecting means such as an interlocking threading or detent fit mechanism. In this embodiment the upper and lower rings can be opened or disconnected to allow insertion and removal of the sheet, and juxtaposingly closed, eg., by a snap 72 on one ring adapted to form a detent fit within a receptacle 74 on the opposing ring, thereby holding the sheet in a fixed position between the two rings. To facilitate this purpose, opposing faces 75 of the upper and lower rings may have a rugose or otherwise decorated surface to facilitate retention of the sheet, for example a ridge 76 or ridges to engage the sheet and securely clamp the sheet between the two rings.

In an alternative design depicted in FIGS. 4 and 5, there is no upper retaining ring 72 and the sheet 38 simply rests upon the support member 56 or is removably retained against an upper surface 76 of the support member by alternative retaining means. For example, the sheet may be fitted within a recess 78 surrounding the upper surface of the support member that is shaped and dimensioned to receive the sheet. The sheet may be securely fitted within the recess, eg., by appropriately sizing the sheet so an edge of the sheet frictionally engages a sidewall 79 of the recess. Alternatively, a retaining groove may be provided between the sidewall of the recess and the upper surface of the support member to receive the edge of the sheet and thereby retain the sheet by a detention fit within the recess during use. In yet another alternative design, the sheet simply rests atop the upper surface of the support member and is removably secured thereto, eg., by wetting or gluing (preferably with an inert bonding agent) to create a temporary bond between the sheet and upper support member surface. In each of the foregoing designs, the sheet can be easily seated within or atop the housing for sample collection and removed thereafter for processing, eg., by hand or using forceps or other conventional handling tools.

In preferred embodiments of the invention, the support member 56 includes a recess 78 which forms a fluid-retaining well, as shown in FIG. 5. The recess can thus be filled with a desired solution, such as a buffer, a solution containing a probe, cross-linking agent, blocking agent, denaturing agent, etc., to facilitate sample collection, handling, and/or processing.

Where the design of the support member 56 is such that it spans the lumen 58 of the sample collection housing 30, or when the support member contains a recess 78 forming a well, it is generally desirable to provide air channels 80 in the support member 56 to allow negative vacuum pressure to pass from the housing through the air channels to the engaging portion 14 of the pump during operation, and to allow venting of the engaging portion and housing to permit disengagement of the engaging portion from the breast 17 after use. Preferably, one or more such air channels are located near the periphery of the support member, as shown in FIGS. 2, 3, 5, 6 and 9. Alternatively, one or more air channels may be centrally located, as shown in FIG. 4. The air channels may be positioned so that they do not communicate with the solid phase sample collection medium, as shown in FIGS. 2, 3, 5, 6 and 9, or they may communicate and form a gaseous connection therewith (provided that the solid phase medium is porous and has sufficient strength to withstand vacuum pressures transmitted through the air channel), as shown in FIG. 4.

Alternative designs and configurations of the housing 30 and/or support member 56 are also provided which vary with the type of solid phase sample collection medium used. For example, when a particulate solid phase sample collection medium 41 (eg. beads, resins, or microspheres) is used, the medium may be enclosed in a cartridge 82 removably mounted to, or integrated within, the support member or otherwise removably connected to the sample collection housing 30. As shown in FIG. 9, preferred embodiments of the invention provide a removable engagement mechanism which allows the cartridge or other receptacle containing the solid phase medium to be removably engaged relative to the housing, eg., by engaging the cartridge with a support member so that a first end of the cartridge makes a fluid connection with the engaging portion 14 of the pump 10. In one embodiment, the first end of the cartridge is removably inserted through a mounting channel 86 which passes through the support member to provide a fluid connection between the engaging portion of the pump and the cartridge first end. Preferably, the channel is dimensioned to receive the first end of the cartridge in a friction fit (eg., wherein a diameter of the channel is about 0.5 mm to 2 cm, preferably about 1 mm to 1 cm, and more preferably about 3–5 mm), whereby the cartridge can simply be pushed into the channel until the cartridge first end is flush with, or extends slightly above, the upper surface 76 of the support member and will remain in place during use. For this purpose it is also preferable to form at least the channel portion of the support member from a resilient, moderately compressible material so that the channel yieldingly receives and releases the cartridge in a moderate (i.e., readily hand removed) friction fit. Alternatively, the cartridge can be engaged relative to the housing by complementary threading or interlocking detent fitting (eg., a conventional key and groove design) between the cartridge first end and the support member channel). In yet other alternative designs the cartridge can be permanently engaged with the support member or engaged directly to the housing.

Design and construction of the cartridge 82 will vary depending on the characteristics of the particulate solid phase medium used, including the size of the particles, the function of the particles (eg., chromatography adsorption, affinity binding, etc.), and whether the particles are used dry or are contained in a solution, among other factors. Design and construction of the cartridge will further depend on the type of breast disease marker(s) which may be sought for detection in the sample (eg., cells, proteins, lipids or nucleic acids).

In a preferred embodiment shown in FIG. 9, the cartridge is cylindrical and contains beads or microspheres. To enclose the beads or microspheres in the cylinder while maintaining a fluid connection with the engaging portion 14 of the pump 10, the first end 84 of the cylinder is covered by a semi-permeable cover 90 of a porous barrier material (eg., a filter or membrane) which allows breast fluid (including or excluding selected components of the fluid, such as cells) to pass through the cover to contact the beads or microspheres, while preventing escape of the beads or microspheres from the cartridge. In this manner, the cover can partition components of the breast fluid into the cartridge, and can also separately retain different components on the cover, thereby allowing for collection of different samples simultaneously. The semi-permeable cover can be affixed to the cartridge by a variety of means, eg., by bonding with a removable or permanent bonding agent, or by providing a removable or integral cover retaining ring 92 to secure the cover to the cartridge first end 84. A second end of the cartridge features a second end cover 96 which may be integral to or removable from the cartridge, and which may be impermeable to gas and fluids or semi-permeable as described above for the first end cover. In another aspect of the invention, the housing 30 supports a non-particulate solid template for sample collection. This type of solid phase collection medium includes, eg., one or more capillary tubes 42 (FIG. 6), coated tubes 43 (FIG. 10), plates, wells, slides and the like. These templates for receiving, adsorbing or binding a sample of breast fluid (or desired components thereof) are preferably formed of glass, plastic or like materials known in the art to be suitable for sample collection (eg., inert plastics).

To accommodate these various templates, yet additional alternative designs and configurations of the housing 30 and/or support member 56 are provided. For example, when capillary tubes 42 are used, these may be mounted to or integrated within the support member, or anchored by a variety of other comparable means with respect to the housing 30. As shown in FIG. 6, preferred embodiments of the invention utilize a support member with one or more mounting channels 86 to removably receive a first end of one or more capillary tubes 42, so that the end of the tube makes a fluid connection with the engaging portion 14 of the pump 10. Thus, the channels have a preferred diameter equal to or slightly less than a diameter of a standard capillary tube, i.e., about 0.5 mm to 3 mm, preferably about 1–2 mm and more preferably about 1.5 mm. Construction of the support member and mounting of the tube(s) is similar to support member construction and mounting of the cartridge as described above. When a single tube is used, it is preferably placed centrally relative to the housing. When multiple tubes are used they may be arrayed to collect multiple samples simultaneously, eg., as shown in FIG. 6.

Another alternative solid template for sample collection provided within the invention is a coated tube 43 which is preferably mounted relative to the housing 30 in the same manner as described above for capillary tubes 42 (FIG. 10). The tube may be open at both ends, or may have a semi-permeable cover at one or both ends, as well as an impermeable second end cover, as described above for the cartridge 82.

The coated tube has a lumenal coating 100 adapted for adsorbing, binding, partitioning or otherwise processing the breast fluid sample. For example, the coating may be an affinity coating having an antibody, ligand, or other binding partner that specifically binds a selected breast disease marker, wherein the coating is covalently or otherwise bound to a lumenal wall of the tube. A wide variety of useful coatings are disclosed herein or are otherwise well known in the art. These coatings may also be used to coat other solid phase media for use within the invention, including templates such as wells, plates, slides, etc, including a well formed by a recess 78 in a support member 56.

Because only small droplets of breast fluid will typically be expressed at the surface of the nipple 16, it is generally preferred to directly contact the expressed fluid on the nipple with the solid phase sample collection medium. This requires positioning of the sample collection medium close to the base 22 of the breast engaging portion 14 of the pump as shown in the figures. Thus, when a support member 56 is provided it is positioned so that its upper surface 76 will directly contact the nipple during application of negative pressure through the engaging portion to the breast. Only approximate positioning is generally required in this regard, because the nipple will tend to be drawn toward the support member by the vacuum and thereby will abut the upper support member surface.

However, because breast pump designs and breast anatomy vary significantly, it is preferable to adjustably mount the solid phase medium relative to the housing 30 so that it can be moved closer to, or farther away from, the base 22 of the engaging portion 14 of the pump 10. Thus, in preferred embodiments of the invention a reciprocating mechanism is provided which adjustably moves the solid phase collection medium in closer, or more distant, proximity to the nipple when the breast pump is engaged therewith. At the beginning of the fluid expression procedure, the collection medium is retracted away from the nipple while negative pressure is applied to the breast to facilitate fluid expression. Fluid expression is visualized through a transparent engaging portion or housing, and the collection medium is then advanced proximal to the nipple to contact the expressed fluid.

Figure 11:
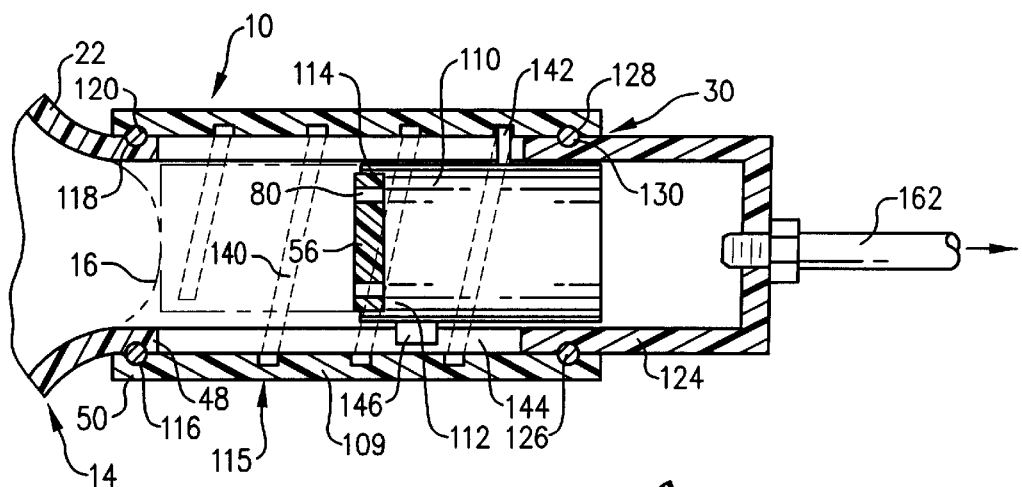
FIG. 11 is a partial sectional view of a breast pump employing a reciprocating mechanism to adjust positioning of a solid phase sample collection medium within the pump.

As shown in FIG. 11, a preferred design for the reciprocating mechanism incorporates a support member 56 to support the solid phase collection medium, as described above. The support member is reciprocatingly mounted relative to a rotating member 109 of the housing 30, preferably on a reciprocating carrier 110. The support member may be removably mounted to the carrier, eg., by friction fitting, detention fitting or threadedly engaging the support member to a first end 112 of the carrier, as described above for mounting the support member to the housing and/or engaging portion 14 of the pump 10. For example, the support member may be mounted by friction fitting within a circumferential groove 114 at the first end of the carrier. In conjunction with this design, the carrier is preferably in the form of an open cylinder so that negative pressure can be effectively transmitted through the carrier and support member to the engaging portion.

To reciprocatingly adjust the position of the carrier 110 and/or support member 56 relative to the engaging portion 14 of the pump 10, the rotating member 109 of the housing 30 is sealably, rotatably, and removably interconnected to the base 22 of the engaging portion. This interconnection may be accomplished by a variety of designs, one of which is to seat a first O-ring 116 in opposing circumferential grooves 118, 120 in the connecting ends 48, 50 of the engaging portion, and the rotating member of the housing, respectively. These grooves are sized and dimensioned to receive the O-ring in an airtight seal when vacuum pressure is applied through the housing and engaging portion of the pump, without substantially compressing the O-ring. The O-ring is also lubricated, eg., with silicon grease. These features allow free rotation of the rotating member of the housing relative to the engaging portion of the pump, which rotation drives the reciprocating mechanism to advance the sample collection medium (eg., by advancing the carrier and/or support member) to contact the expressed breast fluid on the nipple 16.

To complete the reciprocating mechanism for the above described embodiment of the invention, the rotating member 109 of the housing 30 is also sealably and rotatably interconnected to a stationary member 124 of the housing. This interconnection is preferably achieved by seating a second O-ring 126 in opposing circumferential grooves 128, 130 in a rear connecting end 132 of the rotating member of the housing and a front connecting end 134 of the stationary member 124 of the housing, respectively. These grooves are also sized and dimensioned to receive the O-ring in an airtight seal without substantially compressing the O-ring, and the O-ring is lubricated to facilitate free rotation of the rotating member relative to the stationary member.

To reciprocate the carrier 110 and/or support member 56 forward and backward relative to the engaging portion 14, the rotating member 109 of the housing 30 is provided with a lumenal, helically oriented groove 140 dimensioned to receive a riding peg 142 extending transversely from the carrier or support member. In addition, the rotating member of the housing is provided with a longitudinally oriented, lumenal groove 144 dimensioned to receive an angularly fixating keel 146 extending transversely from the carrier or support member. In accordance with this design, rotation of the rotating member 109 of the housing 30 drives rotation of the carrier or support member which is angularly fixed relative to the rotating member by the fixating keel engaged with the longitudinal groove of the rotating member. As the rotating member of the housing and carrier thus rotate (with the position of the engaging portion and stationary member of the housing angularly fixed by friction or manual or structural resistance), the riding peg rides along the helical groove, translating the peg in the direction of the groove and thereby causing the support member or carrier to reciprocate forward or backward relative to the engaging portion.

To insert and remove the solid phase medium and/or support member 56 from the rotating member 109 of the housing 30, a removable interconnection is provided between the rotating member and the base 22 of the engaging portion, as described above. To uncouple the rotating member and engaging portion, all that is required is that these parts be pulled in opposing directions, whereby the O-ring 116 will unseat from one of the opposing circumferential grooves 118, 120 in the connecting ends 48, 50 of the engaging portion and rotating member, respectively. To recouple the rotating member and engaging portion after loading or retrieval of the sample collection medium and/or support member, they are simply pushed back together. To facilitate reseating of the O-ring, it may be desired to make one of the opposing circumferential grooves deeper than the other, so that the deeper groove retains the O-ring when the rotating member and engaging portion are separated, and the shallower groove more readily accepts the O-ring when they are re-coupled.

Figure 14:
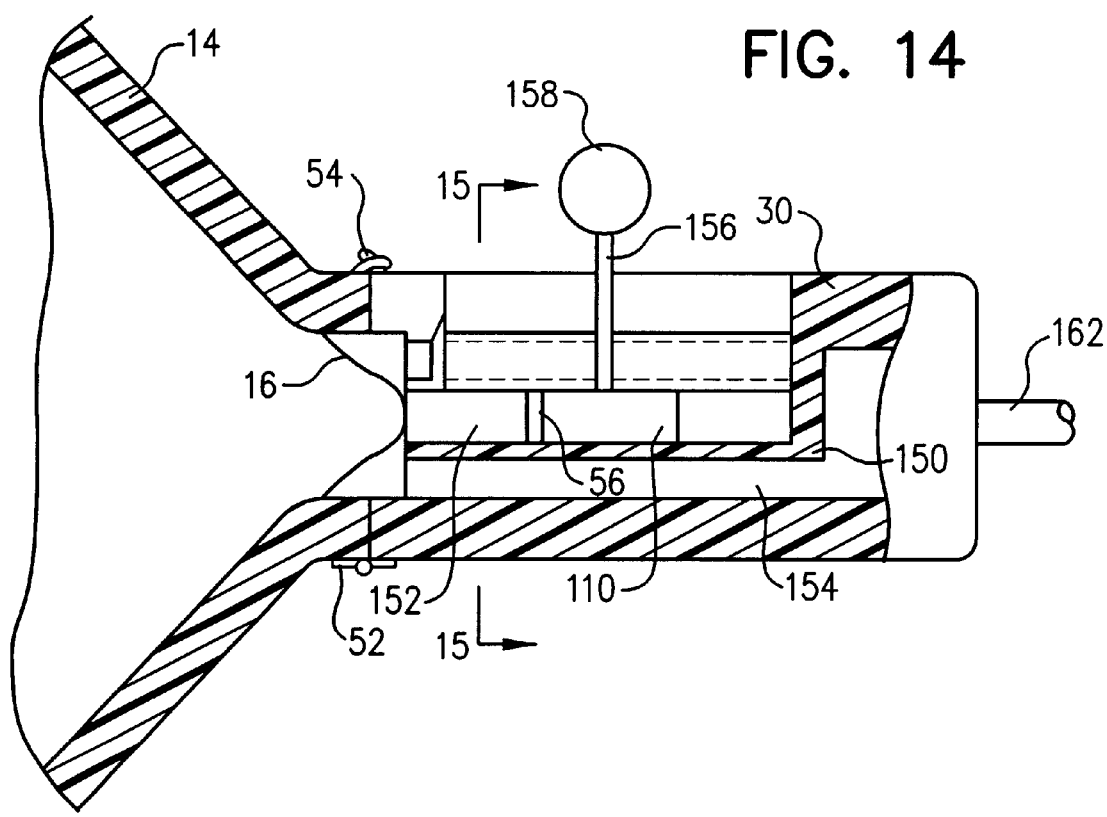
FIGS. 14 and 15 provide partial sectional views of a breast pump employing a sliding reciprocating mechanism to adjust positioning of a solid phase sample collection medium within the pump.
Figure 15:
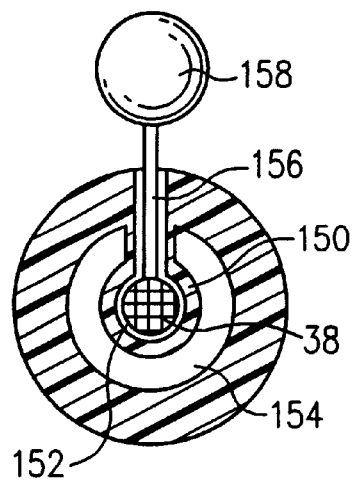

An alternative reciprocating mechanism is provided within the invention which uses a simple slide mechanism to reciprocate the sample collection medium relative to the engaging portion 14 of the pump 10, as shown in FIGS. 14 and 15. One embodiment of the slide mechanism features a manifold 150 defining an inner lumen 152 which is not in gaseous connection with an outer lumen 154 of the housing. This design provides for a manual slide lever 156 to extend to the outside of the housing so that a head portion 158 of the lever can be manually engaged by a pump operator. The slide lever is in turn connected to the support member 56 or carrier 110 which are sized and dimensioned to allow the carrier to reciprocate freely within the inner lumen.

In operation, the slide lever 156 is moved to a rearward position so that the solid phase sample collection medium (eg., a pad or sheet 38 of absorbent material) is out of contact with the nipple 16, as shown in FIG. 14. Negative pressure is applied through the outer lumen 154 to the area of the breast surrounding the nipple, the tip of which is aligned with the inner lumen. Breast fluid expression is visualized through the transparent engaging portion and housing, at which time the lever is manually engaged by the head portion 158 and moved forward. Movement of the lever causes the support member and/or carrier to move forward until the sample collection medium contacts the expressed fluid at the tip of the nipple. The engaging portion and housing are removably connected, eg., by a hinge 52 and latch 54 or other suitable connection means, thereby allowing for easy insertion and removal of the solid phase medium and/or support member.

In each of the foregoing breast pump designs, the engaging portion 14 of the breast pump 10 is in gaseous connection with a vacuum pump 160 capable of generating sustained negative pressure in an area of the breast 17 surrounding the nipple 16 (see FIG. 1). Any of a large variety of vacuum pumps, which are well known for use in conjunction with breast pumps, can be used, including manual pumps (FIG. 1), mechanically driven pumps and electrically driven pumps. When activated, the pump generates negative pressures of between about 50–200 mm Hg. Typically the pump will be connected via a heavy vacuum hose 162 in connection with the engaging portion. Generally, the hose is connected to the housing 30 which will is in gaseous connection with the engaging portion (see, eg., FIGS. 1, 8 and 11).

Pressure exerted upon the breast 17 by the pump can be varied in accordance with well known pressure modulating mechanisms (eg., by providing a diaphragm or other mechanism to modulate a diameter of an in line, pressure modulating valve). In addition, the breast pump 10 includes a venting mechanism, eg., a pressure release valve 164, which the user can selectively operate to close and vent the system before and after use, thereby selectively applying and releasing the vacuum pressure acting on the breast. In this regard, the system is generally vented as soon as sufficient breast fluid expression is observed by the operator. This also relieves pressure on seals (eg., Q-rings 116, 126), when the reciprocating mechanism relies on a sealable and rotatable connection between different parts of the pump (as in FIGS. 11 and 13), thereby facilitating respective rotation of the different parts to reciprocate the support member 56 and/or carrier 110.

Figure 12:
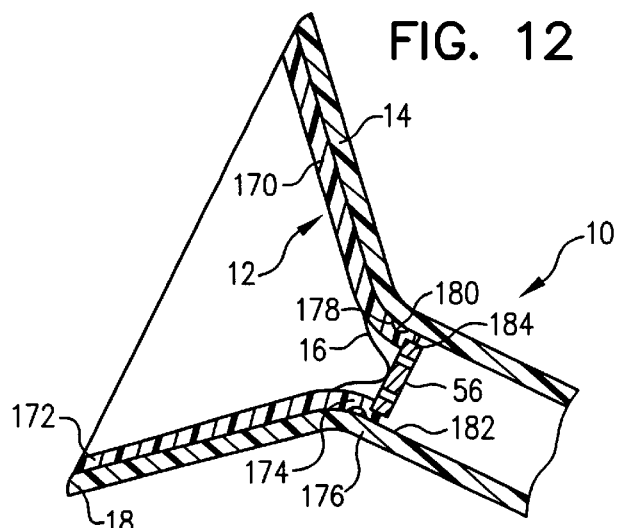
FIG. 12 depicts a breast pump adapter employing the concepts of the invention.
Figure 13:
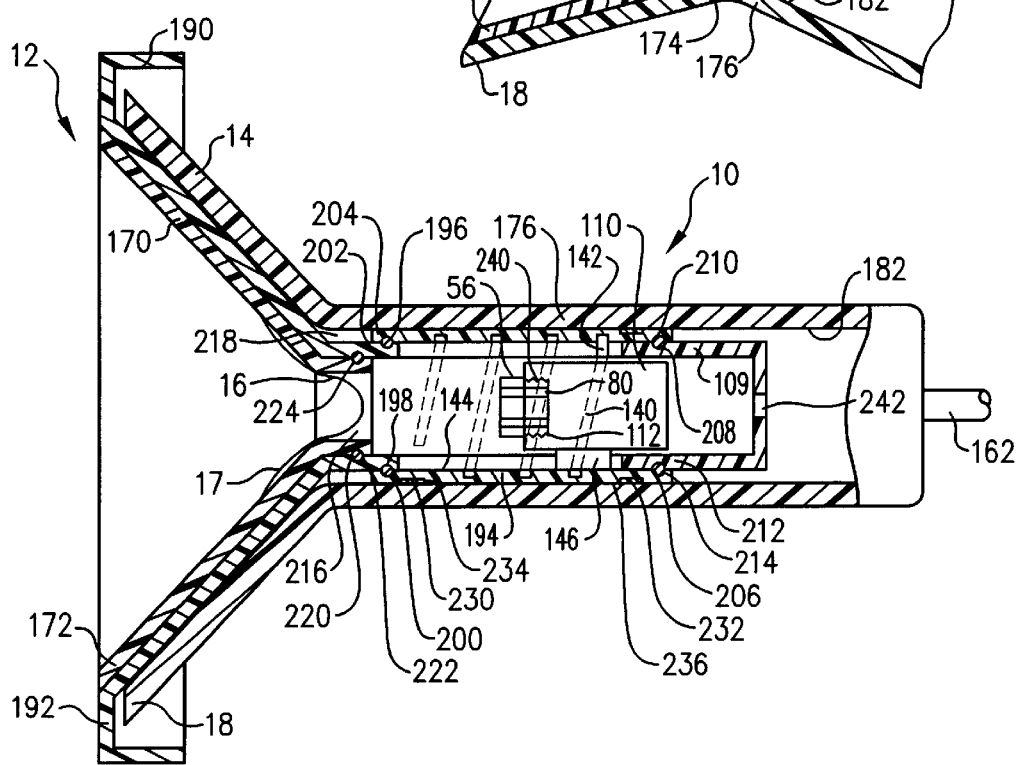
FIG. 13 depicts a breast pump adapter employing a reciprocating mechanism to adjust positioning of a solid phase sample collection medium within the adapter.

In yet another aspect of the invention, a breast pump adapter 12 is provided which couples a solid phase sample collection medium with a conventional breast pump (See FIGS. 12 and 13). As shown in FIG. 12, the adapter features a replacement breast engaging portion 170 sized and dimensioned for removable insertion within a breast engaging portion 14 of a conventional breast pump. In preferred embodiments, the replacement breast engaging portion is funnel shaped and nests within a funnel shaped breast engaging portion of an existing breast pump. When fully nested, a terminal edge 172 of the replacement breast engaging portion extends at least as far as the terminal edge 18 of the breast engaging portion of the existing breast pump.

The replacement breast engaging portion 170 can be removably connected to the breast engaging portion 14 of the existing breast pump 10 by a variety of means, eg., by friction fitting, detention fitting or threadedly engaging the replacement engaging portion with the breast engaging portion of the existing pump. Preferably, the adapter 12 has a stem portion 174 which extends into a cylindrical, connecting portion 176 of the existing pump, and the stem portion cooperates with this part of the existing pump to provide a removable connection mechanism. Thus, in one preferred embodiment the stem portion features a circumferential groove 178 dimensioned to receive an O-ring 180, which O-ring impinges against an inner wall 182 of the connecting portion to create a friction fit to interconnect the replacement engaging portion with the breast engaging portion of the existing pump.

The adapter 12 supports a solid phase sample collection medium in fluid connection with the replacement engaging portion 170. Preferably, the solid phase medium is connected with the replacement engaging portion by a support member 56, as described above. The support member may be integrally or removably mounted to the adapter, eg., by friction fitting, detention fitting or threadedly engaging the support member to the stem 174 of the replacement engaging portion, in a position that will allow contact between the nipple and solid phase medium during or after breast fluid expression. For example, the support member may be mounted by friction fitting within a circumferential groove 184 at a base of the stem (FIG. 12).

In preferred embodiments of the breast pump adapter 12, a reciprocating mechanism is provided to move the solid phase sample collection medium relative to the replacement engaging portion 172, in accordance with the concepts described above. As shown in FIG. 13, a preferred design for the adapter having a reciprocating mechanism features a replacement breast engaging portion 170 sealably and rotatably nested within a rotating dial member 190, which is in turn sized and dimensioned for removable insertion within a breast engaging portion 14 of an existing breast pump. The replacement breast engaging portion and rotating dial member are preferably funnel shaped to collectively nest within a funnel shaped breast engaging portion of a conventional breast pump. When fully nested, a terminal edge 172 of the replacement breast engaging portion and free edge 192 of the rotating dial member extend at least as far as the terminal edge 18 of the breast engaging portion of the existing breast pump.

The rotating dial member 172 is connected to a rotating member 109 of the housing 30, preferably as a unitary insert, whereby manual rotation of the dial member drives rotation of the rotating member of the housing. The rotating member of the housing is in turn rotatably coupled with an anchoring member 194 of the housing which anchors the entire housing within the existing pump, eg., within a cylindrical, connecting portion 176 of the existing pump. As shown in FIG. 13, the anchoring member of the housing is preferably in the form of a sleeve which partially surrounds the rotating member of the housing and is sealably, rotatably connected therewith. The anchoring member is in turn non-rotatingly anchored within the cylindrical, connecting portion of the existing pump.

In one preferred embodiment the rotating member 109 of the housing is sealably, rotatably connected with the anchoring member 194 of the housing by seating a first Q-ring 196 in opposing circumferential grooves 198, 200 at front connecting ends 202, 204 of the rotating member and the anchoring member 194 of the housing, respectively. These grooves are sized and dimensioned to receive the Q-ring in an airtight seal between the rotating member and anchoring member, without substantially compressing the O-ring. The O-ring is also lubricated to facilitate free rotation of the rotating member relative to the anchoring member. A second, lubricated and non-compressingly seated O-ring 206 is seated in opposing circumferential grooves 208, 210 at rear connecting ends 212, 214 of the rotating member and anchoring member of the housing, respectively, to facilitate rotation of the rotating member relative to the anchoring member.

To align and facilitate rotation of the rotating member 109 of the housing, the rotating dial member 190 (which drives the rotating member of the housing) is sealably, rotatably connected with the replacement engaging portion 170 of the adapter 12. Preferably, the replacement engaging portion has a stem 216 which nests within a stem-shaped base 218 of the rotating dial member. Free rotation between these structures is achieved, eg., by providing a third lubricated and non-compressingly seated O-ring 220 seated in opposing circumferential grooves 222, 224 in the stem and base of the replacement engaging portion and rotating dial member, respectively. This rotation is also facilitated by friction contact (by pressure and/or suction) between the replacement engaging portion and the breast 17 of the patient, which angularly secures the replacement engaging portion and prevents its co-rotation with the rotating dial member.

The anchoring member 194 of the housing is in turn anchored within the existing pump by an anchoring mechanism which angularly secures the anchoring member within the pump, eg., against an inner wall 182 of the cylindrical connecting portion 176. For example, front and rear compressible anchoring sleeves 230, 232 may be mounted in front and rear circumferential anchoring sleeve retainer grooves 234, 236 surrounding the anchoring member. The anchoring sleeves are non-lubricated and are made of a semi-compressible material such as rubber or soft plastic. This construction creates a friction anchor between the anchoring member and the inner wall of the connecting portion, so that the anchoring member does not move angularly during rotation of the rotating member 109 of the housing. Both the anchoring sleeves and retainer grooves are preferably sharply angled at a position corresponding to the bases of the retainer grooves (i.e., they have a rectangular or triangular cross-section), to securely retain the anchoring sleeves in the grooves despite strong friction against the inner wall of the connecting portion when the anchoring member of the housing is being inserted into the connecting portion of the existing breast pump 10 to assemble the adapter 12 with the pump.

Because the replacement engaging portion 170 is anchored by friction against the breast 17, and the anchoring member 194 of the housing 30 is anchored by friction against the inner wall 182 of the connecting portion 176 of the existing pump 10, the rotating member 109 of the housing rotates freely with respect to both the replacement engaging portion and the anchoring member when an operator manually engages the rotating dial member 190 and turns it gently while maintaining pressure against the breast.

Relative rotation between the rotating member and anchoring member of the housing drives the reciprocating mechanism within the instant embodiment of the invention to advance the sample collection medium (eg., by advancing a carrier 110 and/or support member 56 supporting the medium) toward the replacement engaging portion 170 to contact the expressed breast fluid on the nipple 16. As with previously described embodiments, the housing 30 preferably houses a support member 56 to support the solid phase collection medium, as described above. The support member is reciprocatingly mounted relative to the anchoring member 194 of the housing 30, preferably on a reciprocating carrier 110. The support member may be removably mounted to the carrier, eg., by friction fitting, detention fitting or threadedly engaging the support member to a first end 112 of the carrier, as described above. In the embodiment shown in FIG. 13, the support member is removably engaged with the carrier by cooperative threading 140 between the support member and carrier. In addition, the support member may be sized and dimensioned for receipt within the stem 216 of the replacement engaging portion, because the replacement engaging portion and an inner (i.e., lumenal) diameter of the stem thereof are smaller than respective dimensions of the original engaging portion 14 and its base 22, so that the nipple may not fully extend through the stem to contact the collection medium within the housing. Also in conjunction with this design, the carrier is preferably in the form of an open cylinder and the rotating member 109 of the housing has a vacuum port 242 so that negative pressure can be effectively transmitted through the rotating member and carrier (and/or through air channels 80 of the support member) to the replacement engaging portion.

To reciprocatingly adjust the position of the carrier 110 and/or support member 56 relative to the replacement engaging portion 170 of the adapter 12, the anchoring member 194 of the housing is provided with a lumenal, helically oriented groove 140 dimensioned to receive a riding peg 142 extending transversely from the carrier or support member. In addition, the rotating member of the housing is provided with a longitudinally oriented, lumenal groove 144 dimensioned to receive an angularly fixating keel 146 extending transversely from the carrier or support member. Lastly, the rotating member is provided with a second, longitudinally oriented, lumenal groove 244 to allow access of the riding peg through the wall of the rotating member of the housing into the helically oriented groove and to allow reciprocating passage of the pin along the groove.

In accordance with this design, rotation of the rotating dial member 190 drives rotation of both the rotating member 109 of the housing 30 as well as the carrier 110 (or support member) which is angularly fixed relative to the rotating member by the fixating keel 146 engaged with the longitudinal groove 144 of the rotating member. As the rotating member and carrier thus rotate (with the position of the replacement engaging portion 170 and anchoring member 194 angularly fixed by friction or manual or structural resistance), the riding peg rides along the helical groove 140, translating the peg in the direction of the groove and thereby causing the support member or carrier to reciprocate forward or backward relative to the replacement engaging portion.

To insert and remove the solid phase medium and/or support member 56 from the adapter 12, removable connections can be uncoupled between the existing pump 10 and the entire adapter unit, between the rotating member 190 and anchoring member 194 of the housing, or between the rotating dial member and replacement engaging portion 170, among other access designs which will be readily apparent to those skilled in the art.

The following examples are offered by way of illustration, not by way of limitation.

EXAMPLE 1
Stimulation of Mammary Fluid Expression by Intranasal Administration of Oxytocin Coupled With Breast Pump Application Oxytocin nasal solution, acts specifically on the myoepithelial elements surrounding the alveoli of the breast and making up the walls of the lactiferous ducts, causing their smooth muscle fibers to contract and thus force any fluids present into the large ducts or sinuses where it can be expressed from the nipple by the further action of a breast pump. The nasal spray is promptly absorbed by the nasal mucosa to enter the systemic circulation. Intranasal application of the spray preparation is a practical and effective method of administration. Half-life of oxytocin in the human circulation is extremely short, approximately 10–15 minutes, and oxytocin is then rapidly removed from plasma by the kidney, liver, and mammary gland.

Because of the known effects of oxytocin to cause uterine contractions, pregnant women should not be treated by the methods contained herein unless the benefits of testing outweigh the risk of inducing premature labor.

The oxytocin nasal solution contains a concentration of natural or synthetic oxytocin, or a functional analog thereof, that is intranasally effective in a selected volume of administered spray to stimulate expression of mammary fluid from a nipple of the patient when a breast pump is applied to the nipple to assist mammary fluid expression. In the present example, a preferred oxytocin preparation containing approximately 40 USP units of oxytocin per ml of lactated Ringer's solution is administered into the nose with the squeeze bottle held in the upright position while the patient is in a sitting position. One or two sprays are administered into each nostril from a standard nasal squeeze bottle, which delivers approximately 0.5 ml of the oxytocin solution per spray in a fine mist when the bottle is squeezed. The number and volume of sprays administered, as well as the concentration of oxytocin in the solution, can be adjusted according to well known pharmacokinetic principles (See for example, Newton, *Ann. N.Y. Acad. Sci.* 652: 481–483; Mena, *Neuroendocrinology* 61: 722–730, 1995; Gonser, *Arch. Gynecol. Obstet.* 256: 63–66, 1995; Orhue, *Obstet. Gynecol.* 83: 229–233, 1994; Satin et al., *Am. J. Obstet. Gynecol.*, 166: 1260–1261, 1992; and Satin et al., *Obstet. Gynecol.* 83: 234–238, 1994, each incorporated herein by reference in its entirety) to ensure that the amount of oxytocin administered to the patient corresponds to an intranasally effective amount to stimulate the expression of at least 3 $\mu$l of mammary fluid in at least 50% of non-lactating female patients with the aid of the breast pump. For example, adjustments may be desired in the is number of sprays delivered to the patient, and/or the timing of spray delivery, so that the clinician can modulate the dosage to each patient's varying sensitivity, and thereby minimize potential adverse side effects. In the present example, a preliminary dose of a single spray of the 40 Unit/ml oxytocin solution is delivered into each nostril of the patient, and the administering clinician waits for a short post-administration period of 2–3 minutes. After this period the breast pump is applied, and the clinician determines whether or not the amount of oxytocin delivered was sufficient to stimulate breast pump assisted expression of mammary fluid. If no fluid is expressed at this stage a booster dose of 1 or 2 additional sprays of the oxytocin solution is administered in each nostril, and the pump is reapplied after a 5–10 minute post-booster administration period.

After the intranasally effective dose of the oxytocin is administered and the clinician has allowed a suitable post-adminsitration period to elapse for the oxytocin to reach and stimulate the target alveolar-ductal tissue, the breast pump is applied according to well known procedures. Negative pressures of 50–200 mm Hg are applied in the area of the nipple and are maintained, intermittently or continuously, for approximately 1–15 minutes, depending on the sensitivity of individual patients, oxytocin dosage and other factors. Alternatively, oxytocin can be administered by intramuscular or intravascular routes by well known means (Oxytocin Injection (synthetic), USP; Wyeth-Ayerst Laboratories) to effect the same response as intranasal administration.

Using the above methods, primary samples of mammary fluid containing at least 3 $\mu$l of fluid are expressed by 50% or more of non-lactating female patients. During or after the mammary fluid expression step, a biological sample is collected from the expressed mammary fluid. In the present example, a nitrocellulose filter is placed within the breast pump in line with a path of the expressed mammary fluid into the pump, so that the expressed fluid contacts the filter. Upon contact of the primary sample of expressed mammary fluid with the filter, cells, proteins and other desired components of the mammary fluid adhere to the filter to form a filter-bound biological sample for subsequent analysis. Other suitable biological samples, including whole mammary fluid samples, cytological samples of whole cells, membranes or other cellular components, and samples containing proteins, glycoproteins, peptides, nucleotides and other constituents of the primary mammary fluid sample can be collected with appropriate modifications of the above procedures, according to well known principles and methods.

EXAMPLE 2
Verification of Sample Origin and Quality Using Lysozyme Analysis

To ascertain that the primary sample of mammary fluid, or the collected sample, obtained by the above methods is of mammary origin and is not corrupted by likely contaminants, one or more constituents of normal mammary fluid are assayed for. In the present example, an enzyme that is ordinarily present in mammary fluid, lysozyme, is assayed in the primary mammary fluid sample to help confirm that the sample is of mammary origin. Lysozyme (muramidase) is an enzyme which hydrolyzes beta 1,4-glycosidic linkages in the mucopolysaccharide cell wall of a variety of microorganisms, which activity can be readily detected and quantified using a routine, inexpensive assay. In the present example, Lysozyme is measured in the primary mammary fluid sample using the Quantiplate Lysozyme Test kit (Kallestad, Chasta, Minn.). The assay employs the reagents and procedures provided by the manufacturer and specified in detail in the manufacturer's instructions, with the exception that a mammary fluid sample is substituted in place of serum, urine or tears. Analysis of these results establishes that the sample contains lysozyme, which is a normal component of human serum, urine, saliva, tears, nasal secretions, vaginal secretions, seminal fluid, and mammary fluid.

More specific assays are used in place of the lysozyme assay, or to supplement lysozyme assay results, particularly where clinical data for human patients are being gathered. Other mammary fluid markers for sample verification that are more specific than lysozyme can be readily incorporated within the invention, based on published and generally known information. In one example, the presence of cathepsin D is assayed using the monoclonal antibodies and methods disclosed in Vetvicka et al., *Biochem. Mol. Biol. Int'l.* 30: 921–928, 1993, incorporated herein by reference in its entirety). In another example, one or more human mammary epithelial antigens (HME-Ags) corresponding to glycoprotein components of the human milk fat globulin (HMFG) protein are detected in the primary mammary fluid sample, or in the biological sample that is used in the breast cancer marker assay, using specific antibody probes, as described by Rosner et al., *Cancer Invest.* 13: 573–582, 1995; Ceriani et al. *Proc. Natl. Acad. Sci. USA* 74: 582–586, 1982; Ceriani et al., *Breast Cancer Res. Treat.* 15; 161–174, 1990, each incorporated herein by reference in its entirety). In many cases, the sample verification assay can be incorporated within the breast cancer marker assay in a single procedure, for example as described below in Example 4, an assay for HME-Ags (wherein the HME-Ag findings are indicative of sample origin/quality, and also of the presence and/or quantity of a specific breast cancer marker in the sample). In another example, sample verification is achieved through a combinatorial (i.e. multiple marker) immunoassay targeting various cytokeratins, which can be detected as a panel of cytokeratins specifically expressed in mammary tissue sample. (See, Nagle, *J. Histochem. Cytochem.* 34: 869–881, 1986, incorporated herein by reference in its entirety). One or more of these cytokeratins (eg. K5, K8, K18 and K19) can be simultaneously or independently measured in the context of a breast cancer assay, and the level of expression of the subject cytokeratin(s) can yield information concerning the presence or status of breast cancer in a patient. (See for example, *Focus*, Harvard University News Office, Mar. 21, 1991, pp. 2–3; and Lee, *Proc. Natl. Acad. Sci.* 88: 1991, each incorporated herein by reference in its entirety).

EXAMPLE 3
Cytology in Biological Samples From Mammary Fluid

This example describes the use of conventional cytological techniques to identify and classify breast diseases from samples obtained as described in Example 1.

Following collection of the sample in the sample collector, the central region of a clean glass microscopic slide is touched to the sample and a cover slip is slid over the sample to spread it along the surface of the slide. The slide is allowed to air dry and then is fixed, for example in absolute alcohol, and stained with standard cytological stains, such as methylene blue, hematoxyln and eosin, and other suitable stains.

The slides are then examined by light microscopy for evidence of atypical growth of cells and clumps of cells, using well known methods, including those described in *Diagnosis of Non-Palpable Breast Lesions: Ultrasonographically Controlled Fine-Needle Aspiration: Diagnostic and prognostic Implications of Cytology* by Jacqueline Mouriquand, published by S Karger Pub: July 1993, ISBN: 3805557477; *Breast: Guides to Clinical Aspiration Biopsy* by Tilde S. Kline, Irwin K. Kline, published by Igaku-Shoin Medical Pub: May 198g, LSBN: 0896401596; *Cytopathology of the Breast* (*Asop Theory and Practice of Cytopathology;* 5 by Shahla Masood, published by American Society of Clinical Pathology: November 199S, ISBN: 0891893806; *Fine Needle Aspiration Cytology and Its Clinical Applications: Breast and Lung* by Philip S. Feldman, published by American Society of Clinical Pathology: November 1984, ISBN: 0891891846, each incorporated herein by reference in its entirety.

EXAMPLE 4
Immunoassay for Human Mammary Epithelial Antigens in Biological Samples From Mammary Fluid Human mammary epithelial antigens (HME-Ags) are glycoprotein components of the human milkfat globule (HMFG) and of the membrane of the breast epithelial cell, which are released by breast tumors and not by normal breast tissue. (Ceriani et al., *Proc. Natl. Acad. Sci.* 74: 582–586, 1977, incorporated herein by reference in its entirety). In the present example, several HME-Ags, having molecular weights of 150, 70, and 45 kilodaltons, are detected and measured using specific anti-HMFG or anti-human mammary epithelial (α-HME) probes prepared and employed as described by Ceriani et al., *Proc. Natl. Acad. Sci.* 79: 5420–5425, 1982 (incorporated herein by reference in its entirety).

To begin the assay, biological samples from mammary fluid collected on nitrocellulose filters are eluted electrophoretically into phosphate buffered saline to provide a test sample, according to standard methods. Alternatively, whole mammary fluid or other types of biological samples obtained from mammary fluid can be constituted in an appropriate medium or mixture to provide a test sample for the assay. Once the test sample is thus provided, it is then assayed according to the HME-Ags radioimmunoassay (RIA) methods described in Ceriani et al., *Breast Cancer Res. Treat.* 15: 161–174, 1990 (incorporated herein by reference in its entirety).

Briefly, the RIA includes two preliminary treatments of the biological samples to separate interfering factors: a centrifugation step to separate out any fat present, and a second, precipitation step to precipitate potential immuno-complexes using polyethyleneglycol (PEG). The next steps comprise the assay proper, where HMFG antigen bound to a solid support (microtiter plates) is presented to stoichiometric or lesser amount of the α-HME antibody probe, and binding of the α-HME is competed by the biological samples from mammary fluid preliminarily treated as above. The amount of α-HME bound to HMFG antigen on the solid phase is determined in a final step by detection of the α-HME antibody probe by radioiodinated, affinity-purified rabbit anti-mouse immunoglobulin.

Solutions used in the assay are as follows: i) Phosphate buffered saline (PBS): 176 ml 0.05M $KH_2PO_4$, 608 ml 0.05M $Na_2HPO_4$, and 8 g NaCl brought up to 1000 ml in $H_2O$ (pH7.4). ii) RIA buffer: 0.1% BSA, in 0.3% Triton-X-100 (Research Prod. International Corp., Mount Prospect, Ill.) plus 0.05% sodium azide in PBS. iii) Detergent buffer: 0.3% Triton-X-100 plus 0.05% sodium azide in PBS. iv) Buffered polyethylene glycol (PEG): 6.6% PEG (M.W. 8000) (Sigma) plus 0.05% sodium azide in PBS) $^{125}$I-labeled affinity-purified rabbit anti-mouse immunoglobulin (Rα-mouse Ig) (Antibodies, Inc., Davis, Calif.), radioiodinated by the chloramine-T procedure as reported (Ceriani et al., *Proc. Natl. Acad. Sci.* 79: 5420–5425, 1982) and diluted to $4 \times 10^6$ cpm/ml, in RIA buffer. Rabbit polyclonal anti-HMFG antibodies or rabbit anti-human mammary epithelial antibodies (α-HME) were prepared and assayed as described (Id.).

To prepare a standard curve for evaluating assay results, control samples from normal human mammary fluid (exposed to nitrocellulose filters and eluted in the same manner as the nitrocellulose adsorbed, eluted test sample, or alternatively provided as normal whole mammary fluid or other selected type of sample obtained from normal mammary fluid, constituted in an appropriate medium or mixture to provide a suitable control assay sample) are centrifuged for 7 min at 10,240 rpm at 10° C. The upper white band formed at the top of the sample (if there is one) is discarded. Fresh 100 pg protein/ml solution of lyophilized dilipidated HMFG (Ceriani et al., *Proc. Natl. Acad. Sci.* 74: 582–586, 1977) in detergent buffer is prepared and sonicated at 10 second intervals for a total of 4 minutes (10 sec. of sonication, followed by a 10 sec. silent period) using a double step micro tip horn at 25 watts on a Sonifier Cell Disrupter 185 (Branson, Danbury, Conn.) at 4° C. HMFG solutions at concentrations of 0, 10, 33.3, 100, 333.3, and 1000 ng protein/ml are prepared in spun female sera, and 3 aliquots of 180 µl of each HMFG level in normal female sera are pipetted into 400 µl polyethylene microcentrifuge tubes (West Coast Sci. Emeryville, Calif.). 150 µl of 6.6% PEG solution is added to each microcentrifuge tube, and the tubes are incubated overnight on a rotating shaker at room temperature.

Test samples are processed in a comparable manner, by centrifuging 300–350 µl of the eluted nitrocellulose filtrate in solution (or, alternatively, of mammary fluid or other assay sample alternative) in a 400 µl microcentrifuge tube for 5–7 min. at 10,240 rpm at 10° C. The microcentrifuge tubes are then cut with a razor blade below the white band formed by the sera (if there was one) and 180 µl of remaining sera is transferred to a new microcentrifuge tube. 150 µl of a 6.6% PEG solution is then added to each microcentrifuge tube, and the tubes are incubated overnight on a rotating shaker at room temperature.

Day Two (1) α-HME is diluted to its appropriate concentration in detergent buffer. The antibody solution has stoichiometric or lesser amounts of α-HME to 6 ng HMFG protein equivalent (prot. eq.). Six ng of HMFG is covalently bound to microtiter plates by the methylated BSA procedure previously described by Ceriani, In: Kennet et al., (eds) *Monoclonal Antibodies and Functional Cell Lines*, Plenum Press, New York, 1984, pp. 398–402, incorporated herein by reference in its entirety.

(2) To process test samples and control samples on the second day, microcentrifuge tubes are centrifuged for 7 min. at 10,240 rpm at 10° C. in a SHMT rotor with a Sorvall RC5C centrifuge. In triplicate, 55 µl of supernatant is pipetted into empty microtiter plate wells (Dynatech, Alexandria, Va.), and any precipitate pelleted is left undisturbed. 25 µl of 6.6% PEG solution is added to each well. 30 µl of α-HME diluted in detergent buffer is also added to each well, and a non-porous Scotch® tape is placed over the wells to avoid evaporation. The microtiter plate is then incubated overnight at room temperature on a rotary shaker.

Day Three

The microtiter plates are centrifuged (3000 r.p.m.) for 30 minutes at room temperature to decant suspended perceptible matter.

50 µl of RIA buffer is added to wells of microtiter plates containing 6 ng HMFG and aspirated off after 5 minutes.

The total contents of microtiter plates from 1), save for any precipitation induced by the PEG and already pelleted, are carefully transferred to the wells of another set of microtiter plates containing 6 ng HMFG per well (Day 2,1), above.

The microtiter plates are incubated for 3 hours with rotating agitation at room temperature.

The plates are washed 5 times with RIA buffer using Dynadrop SR-1 automatic dispenser form Dynatech.

50 µl of the radioiodinated affinity-purified rabbit anti-mouse immunoglobulin diluted in RIA buffer is then adder per well.

The plate is covered with tape and incubated with rotating agitation for 2 hours at room temperature.

The plate is washed 5 times with RIA buffer.

Wells are cut and counted in a gamma counter.

The results of these assays will yield important information concerning the presence and/or status of cancer in patients, comparable in scope and value to the data provided by serum assays conducted for the HME-Ag breast cancer marker by Ceriani et al., *Breast Cancer Res. Treat.* 15: 161–174, 1990. By selecting patient and control samples and developing and evaluating comparative data according to the procedures followed by Ceriani and his coworkers, the assay methods of the invention will also be readily adapted for use in direct clinical applications to determine both prognostic and treatment related variables in breast cancer patients. Reagents and conditions for the assays can of course be substituted or adjusted depending on a variety of anticipated variables, by applying well known immunological methods and principles.

EXAMPLE 5

Competitive Radioimmunoassay for Non-Penetrating Glycoprotein in Biological Samples From Mammary Fluid This competitive radioimmunoassay is based on the displacement by breast epithelial antigens contained in biological samples from mammary fluid obtained according to the methods of the invention of the binding of stoichiometric or lesser quantities of the monoclonal antibody Mc5 to a solid-phase-bound antigen known as non-penetrating glycoprotein (NPGP) contained in HMFG. HMFG is bound to a solid support and exposed to the Mc5 antibody during an incubation period allowing the antibody to bind the NPGP antigen in solid phase-bound HMFG. The presence and/or level of NPGP in the biological sample is ultimately examined by ability of the sample to compete for Mc5 binding to the NPGP antigen in the solid phase-bound HMFG, as detected and/or measured using a radiolabeled goat anti-mouse antibody to bind and label the Mc5 antibody probe.

Buffer and other solutions and reagents in this example are generally the same as those used for the HME-Ags polyclonal antibody radioimmunoassay described in Example 4, above. To provide test samples for the assay, biological samples from mammary fluid contained on nitrocellulose filters are eluted electrophoretically into phosphate buffered saline, according to standard methods. Alternatively, whole mammary fluid or other types of biological samples obtained from mammary fluid can be constituted in an appropriate medium or mixture to provide a test sample for the assay. Once the test sample is thus provided, it is then assayed according to the NPGP/Mc5 radioimmunoassay (RIA) methods described in Ceriani et al., *Breast Cancer Res. Treat.* 15: 161–174, 1990 (incorporated herein by reference in its entirety), as follows:

400 µl of pooled normal female mammary fluid (exposed to nitrocellulose filters and eluted in the same manner as the nitrocellulose adsorbed, eluted test sample, or alternatively provided as normal whole mammary fluid or other types of biological samples obtained from normal mammary fluid constituted in an appropriate medium or mixture to provide a test sample) to provide a suitable control sample, which is diluted to 2.4 ml using RIA buffer at a 1:6 concentration.

A 500 µg/ml solution of lypholized HMFG is prepared in 1×PBS with 0.3% Triton-X-100, 0.05% sodium azide, and sonicated using a double step micro tip horn at 25 watts on a Sonifier Cell Disrupter 185 (Branson, Danbury, Conn.) for 4 minutes (10 sec. sonication, 10 sec. silent period, at 4° C.).

Solutions to prepare a standard curve are prepared using the 2.4 ml 1:6 normal female serum and increasing amounts of HMFG (0, 0.25, 2.5, 25, 50 pg/ml HMFG, as described above in Example 4).

Each test assay sample is diluted 1:6 with RIA buffer (40 µl of serum to 200 µl RIA buffer) to form a diluted test assay sample, and vortexed.

Mc5 stock solution is prepared so that it contains less than stoichiometric amounts of antibody to 100 ng protein/well of HMFG covalently bound to microtiter plates prepared as previously described by Ceriani, In: Kennet et al., (eds) *Monoclonal Antibodies and Functional Cell Lines*, Plenum Press, New York, 1984, pp. 398–402, incorporated herein by reference in its entirety 200 µl RIA buffer are added to each well of 100 ng HMFG and then aspirated after 5 minutes.

To prepare a standard curve, 30 µl of HMFG standardizing solutions (as in 3 above) are added in quadruplicate to a 100 ng protein/well HMFG microtiter well.

30 µl of diluted test assay sample (or, alternatively, of mammary fluid or other assay sample alternative) are added in triplicate to 100 ng/well HMFG microtiter wells.

To each well 20 µl of the Mc5 stock solution is added.

Microtiter plates are covered with nonporous Scotch® tape and incubated overnight at room temperature on a rotating agitator.

The next day the wells are aspirated and washed 5 times with RIA buffer.

To each well 50 µl of 200,000 cpm/50 µl $^{125}$I-goat anti-mouse antibody are dispensed. The wells are covered with nonporous tape and placed on a rotating agitator for 3 hours at room temperature.

Wells are washed 5 times with RIA buffer.

Each well is cut and the radioactivity is counted using a gamma counter.

The results of these assays will yield important information concerning the presence and/or status of cancer in patients, comparable in scope and value to the data provided by serum assays conducted for the NPGP breast cancer marker by Ceriani et al., *Breast Cancer Res. Treat.* 15: 161–174, 1990. By selecting patient and control samples and developing and evaluating data according to the well known procedures followed by Ceriani and his coworkers, the assay methods of the invention will be readily adapted for use in direct clinical applications to determine both prognostic and treatment related variables in breast cancer patients. As will be understood by those skilled in the art, reagents and conditions for the assays can be substituted or adjusted depending on a variety of anticipated variables, according to well known immunological methods and principles.

EXAMPLE 6
Solid Phase Immunoassay for Mucinous Carcinoma Associated Antigen in Mammary Fluid This example uses a sensitive, solid phase immunoassay to detect the mucinous carcinoma associated antigen (MCA) in biological samples from mammary fluid obtained according to the methods of the invention. MCA concentrations are determined using an antibody-bead immunoassay kit provided by Hoffman-La Roche (Basel, Switzerland), and using the reagents and procedures provided by the manufacturer and described in further detail in Eskelinen et al., *Anticancer Res.* 9: 437–440, 1989. Briefly, test assay samples of whole mammary fluid and standards are first incubated with MCA monoclonal antibody beads and then, after appropriate washings, enzyme (horseradish peroxidase) labeled secondary antibody is added. During the second incubation the anti-MCA enzyme conjugates are attached to the antibody antigen complex on the beads.

Excess conjugates are removed by washing and, finally, enzyme substrate are added and the color formed is recorded. The solid phase assay format presented in this example can be adapted for use in a wide array of other assays to detect and/or measure other cancer markers besides the MCA marker, with enhanced sensitivity. In addition, the results of these assays can be evaluated along with those of complementary assays detecting and/or measuring different markers to yield more precise information concerning the presence and/or status of cancer in patients, as exemplified by the combinatorial MCA/CA 15-3 assays described by Eskelinen et al., *Anticancer Res.* 9: 437–440, 1989; see also Eskelinen et al., *Anticancer Res.* 8: 665–668, 1988, each incorporated herein by reference in its entirety.

EXAMPLE 7
Western Analysis of Proteins From Cellular Fractions of Human Mammary Fluid Using Polyclonal and Monoclonal Antibody Probes to Detect Vasopressin A variety of assays are provided by the present invention that focus on cellular samples from human mammary fluid. In general, these assays rely on isolation by standard separation methods (eg. centrifugation, sucrose gradient, etc.) of cells, membranes or other cell components from whole mammary fluid expressed according to the above methods. Biological samples containing whole cells from expressed mammary fluid are particularly useful for cytological and cytochemical examination to detect and evaluate breast cancer in patients. Biological samples containing purified cell membrane fractions from human mammary fluid are particularly useful in this context, for example to detect and/or measure breast cancer markers that are expressed by alveolar-ductal cells as intracellular or membrane bound proteins and are therefore not as readily detected in liquid fractions of mammary fluid as secreted proteins.

The present example focuses on assays for detecting the peptide hormone vasopressin in biological samples from mammary fluid, using methods adapted from North et al., *Breast Cancer Res. Treat.* 34: 229–235, 1995. Specifically, this assay uses a test sample of crude protein isolated from a pooled sample of cells obtained from expressed mammary fluid. The cells are separated from whole mammary fluid according to standard methods, and crude protein is extracted from the cells by sonication in 100 volumes of 0.1 M HCl. The resulting protein suspensions are then centrifuged at 1500×g for 10 min. at ambient temperature, and soluble protein is precipitated with 40% TCA. This protein is pelleted by centrifugation at 10,000×g for 2 min. TCA is then removed from pellets by washing (×2) with ether. Protein is resuspended in 0.1 M Tris HCl (pH8.7), reduced with mercaptoethanol at 100° C. for 5 min. (and in some cases S-alkylated with N-ethyl maleimide), and subjected to SDS-PAGE electrophoresis on 15% gels at pH 9.3 using the method of Laemeli, *Nature* 227: 680–685, 1970, incorporated herein by reference in its entirety. Separated proteins are then electrophoretically transferred with 20 mM Tris glycine (pH 8.0) to Immobilon PVDF membranes (Millipore, Bedford, Mass.). These membranes are blocked with a 5% non-fat milk solution, washed (1×15 min., 2×5 min.) with PBS containing 0.5% Triton, and incubated with preparations of mouse monoclonal antibody to VP-HNP, with rabbit polyclonal antibodies to VP, with rabbit polyclonal antibodies to VAG, or with ubiquitous mouse or rabbit IgG (negative controls) (for description of antibodies and antibody preparation see North et al., *Breast Cancer*

Res. Treat. 34: 229–235, 1995, incorporated herein by reference in its entirety), for 1 h at ambient temperature. Following a second wash in PBS-Triton (1×15 min., 2×5 min.), the membranes are treated, respectively, with goat anti-mouse IgG-horseradish peroxidase conjugate or goat anti-rabbit IgG-horseradish peroxidase conjugate for 1 h, and then washed with PBS-Triton (1×15 min., 4×5 min.). Immunoreactive proteins are visualized using an ECL Western Blotting Detection System with exposure of x-ray film from 10 seconds to 5 min. Prestained SDS-PAGE standard proteins are employed as molecular size markers.

Recent studies suggest that vasopressin is universally expressed in breast carcinoma and is absent from normal breast cells. North et al., *Breast Cancer Res. Treat.* 34: 229–235, 1995. These and other results indicate that vasopressin and its relatives are important breast cancer markers which can be readily detected using immunological assays of proteins isolated from breast tumor cells. Accordingly, the results of the present example using cell samples isolated from human mammary fluid are also expected to yield important information concerning the presence and/or status of cancer in patients.

EXAMPLE 8
Quantification of Carcinoembryonic Antigen in Biological Samples From Mammary Fluid by Dot Immunoblotting Assay Among the more sensitive assays of the invention, useful for measuring low levels of breast cancer markers and for detecting markers when only small volumes of expressed mammary fluid are available, is the dot immunoblotting assay. In the present example, carcinoembryonic antigen (CEA) is measured in whole mammary fluid using an ELMOTECH® anti-CEA monoclonal antibody kit (Mochid Pharmaceutical Co., Tokyo, Japan) in a dot blot assay format. Briefly, anti-CEA monoclonal antibody is diluted to appropriate concentrations and coated on the plastic film. Aliquots (5 $\mu$l) of either standard CEA solution (0, 100, 200, and 500 ng/ml), or of the whole mammary fluid assay sample, are smeared on the immobilized film. Assay standards are prepared from purified antigen preparations, in accordance with the ELMOTECH® kit manufacturer's instructions. If necessary, 1000 ng/ml CEA solution is also used as a standard. After drying at room temperature, the film is exposed to peroxidase-conjugated anti-CEA antibody for 20 min at room temperature. The film is then washed extensively with 1 M saline containing 0.5% (v/v) Tween 20. The enzyme reaction is visualized using tetramethylbenzidine as a chromogen. The developing solution consists of 0.05 mM tetramethylbenzidine and 0.01% hydrogen peroxide in McIlvain buffer (0.1% M phosphate-citrate buffer), pH 5.0, containing 10% methanol. The concentration of CEA in the mammary fluid assay sample is determined by comparing the color intensities with a corresponding standard.

The assay disclosed in the present example, and related assays incorporating antibodies to other tumor markers besides CEA, are particularly useful for measuring low levels of breast cancer markers and for detecting markers in limited sample volumes. The results of these assays will yield important information to determine both prognostic and treatment related variables in breast cancer patients. As will be understood by those skilled in the art, reagents and conditions for the assays can be substituted or adjusted depending on a variety of anticipated variables, according to well known immunological methods and principles.

EXAMPLE 9
Detection of Procathepsin D and Cathepsin D Activity in Biological Samples From Mammary Fluid Cathepsin D is a lysosomal aspartic proteinase which has been studied intensively as a marker for cancer processes necessary for metastasis. In the present example, polyclonal antibodies against procathepsin D are used to immunoprecipitate and immunochemically detect proteins from whole mammary fluid or cell lysates from mammary fluid, generally according to the methods disclosed in Vetvicka et al., *Biochem. Mol. Biol. Int'l.* 30: 921–928, 1993 (incorporated herein by reference in its entirety). Alternatively, or as a complementary assay, the protease activity of cathepsin D is detected, also according to the methods disclosed in Vetvicka et al. (Id.). Briefly, pooled whole mammary fluid (preferably 3 ml if available) is diluted with 3 ml of buffer A (50 mM Tris.HCl, 5 mM $CaCl_2$, 1 mM $MgCl_2$, 500 mM NaCl pH 7.2). The suspension is centrifuged for 30 minutes at 10,000 g. The resulting water phase is centrifuged again under the same conditions. The soluble part (total of approximately 4.5 ml) is loaded on a 1 ml column of Concanavalin A Sepharose (Pharmacia, Uppsala, Sweden) equilibrated in buffer A, and after washing with buffer A the retained proteins are eluted using 0.75 M methyl $\alpha$-D-mannopyranoside. The fractions (250 $\mu$l) are analyzed for cathepsin D activity using the $^{14}C$ hemoglobin assay as described by Lin et al., *J. Biol. Chem.* 264: 4482–4489, 1989 (incorporated herein by reference in its entirety), by western blots and by silver-stained electrophoresis. The inhibition of human milk procathepsin D is accomplished by adding 2 $\mu$l of 1 mM pepstatin A (Boehringer Manheim, Germany) dissolved in methanol to the reaction mixture.

This assay provides but one example of many possible embodiments of the invention that incorporate known biochemical assays, in addition to, or supplemental to immunological assays, to evaluate biological samples from mammary fluid to determine cancer related variables. The fundamental methods provided herein for obtaining samples from human mammary fluid render these assays readily adaptable for widespread clinical application to detect and/ or measure the activity of a subject breast cancer marker within a non-invasive screening protocol.

Those with ordinary skill in the art will appreciate that other embodiments and variations of the invention are possible which employ the same inventive concepts described above. Most particularly, a wide and rapidly expanding array of useful breast cancer markers (including proteins, DNA and RNA sequences and other markers) and probes (including immunological, nucleotide and biochemical probes) are readily available for adaptation and use within the methods and kits of the invention. These markers and probes are described or referenced to a large extent in the literature cited and incorporated within the present disclosure, or are elsewhere published in the literature or well known in the art. Among these known and emerging markers and probes, useful examples within the invention include Her 2 (also known as erbB-2 and neu). Her 2 is a transmembrane glycoprotein growth factor receptor of the EGF receptor family encoded by a gene located on chromosome 17q, a region of frequent amplification in breast cancer cell lines. This marker is highly predictive of breast cancer and can be detected in cellular samples of the invention using known nucleotide probes to detect genetic defects in Her 2, or to detect and/or measure mRNA to determine overexpression of Her 2 linked to increased proliferation of cancer cells. (See for example, Visscher et al., In Weinstein and Graham (eds) *Advances in Pathology* and *Laboratory Medicine*, vol 5, St Louis, Mosby Yuear Book, 1992, pp. 123–161; Barbareschi et al., *Am. J. Clin. Pathol.* 98: 408–418, 1992; Slamon et al., *Science* 235: 177–182, 1987; each incorporated herein by reference in its entirety). Protein levels of Her 2 are also readily detected using available immunological probes. (For review see Porter-Jordan et al., *Hematol. Oncol. Clin. North Amer.* 8: 73–100, 1994 and articles cited on page 80 therein, each incorporated herein by reference in its entirety). Additional markers for use within the invention include EGF and the EGF receptor, for which immunological and non-immunological probes and assay methods readily adaptable within the invention are characterized in detail at page 80–81 of Porter-Jordan et al., *Hematol. Oncol. Clin. North Amer.* 8: 73–100, 1994 and in the references cited therein, each incorporated herein by reference in its entirety. Additional examples of proliferation markers, growth factors and receptors, proteases, adhesion factors, angiogenic factors, oncogenes and tumor suppressor genes that provide useful breast disease markers and probes within the methods and kits of the invention include Ki67 Growth Factor, Cyclin D1, Proliferating Cell Nuclear Antigen, Transforming Growth Factor, Tissue Plasminogen Activator, Insulin Growth Factor Receptors, Collagenase Type IV, Laminin Receptor, Integrins, p53, rb, nm23, ras, c-myc, c-myb, Heat Shock Proteins, Prolactin, Neuron-Specific Enolase, IR-14, KA 1, KA 14, Alpha-Lactalbumin, Actin, IL-10, S-100 protein, Vimentin, Epithelial Membrane Antigen, bcl-2, CA15-3, CA 19-9, Tn Antigen, Alpha-lactalbumin, LASA, Gal-GalNAC, GCDFP-15, Le(y)-Related Carbohydrate Antigen, CA 125, uPA, uPA related antigens and complexes, uPA Receptor, PAl-1 and PAl-2, Betaglucuronidase, CD31, CD44 splice variants, blood group antigens including ABH, Lewis, and MN, and genetic lesions or altered expression levels of CCND1, EMS1, BRCA1 and BRCA2 genes, and many others, for which immunological and non-immunological binding partners, probes and assay methods are known and readily adaptable within the invention. In accordance with the foregoing disclosure, the invention is not to be limited by the exemplary description and drawings herein, but is to be determined in scope by the claims which follow.

We claim:

1. A sample collection device for collecting a biological sample from a mammary organ of a patient, comprising:
   a breast engaging member constructed of a non-porous material sized and dimensioned to receive at least a nipple portion of a breast of said patient and form a suction seal therewith;
   a solid phase sample collection medium in fluid connection with said breast engaging member for receiving a sample of expressed breast fluid; and
   vacuum pump means in gaseous connection with said breast engaging member for generating negative pressure through the breast engaging member to facilitate breast fluid expression, wherein said solid phase sample collection medium is selected from the group consisting of microscopic glass slides, capillary tubes, collection tubes, columns, micro-columns, wells, plates, membranes, filters, resins, inorganic matrices, beads, particulate chromatographic media, plastic microparticles, latex particles, coated tubes, coated templates, coated beads, coated matrices, or a combination thereof.

2. The sample collection device of claim 1, including removable coupling means for removably coupling said sample collection housing with said breast engaging member.

3. The sample collection device of claim 1, wherein said solid phase sample collection medium is supported by a support member integrally or removably mounted within said sample collection housing in fluid connection with said breast engaging member.

4. The sample collection device of claim 3, wherein said support member is disc-shaped and is interposed between said breast engaging member and said sample collection housing.

5. The sample collection device of claim 3, wherein said support member has upper and lower retaining rings and supports a sheet of absorbent or adsorbent material.

6. The sample collection device of claim 3, wherein said support member supports a solid phase sample collection template selected from capillary tubes, coated tubes, columns, micro-columns, plates, wells and microscopic slides, or a combination thereof.

7. The sample collection device of claim 3, wherein said support member defines a fluid-retaining well.

8. The sample collection device of claim 3, wherein said support member includes at least one air channel to allow negative pressure to pass through the air channel to and from said breast engaging member.

9. The sample collection device of claim 1, wherein said solid phase sample collection medium is a particulate medium contained within a cartridge removably mounted within said sample collection housing and having a first end of said cartridge in fluid connection with said breast engaging member.

10. The sample collection device of claim 9, wherein said first end of said cartridge is covered by a porous barrier material.

11. A sample collection device for collecting a biological sample from a mammary organ of a patient, comprising:
    a breast engaging member constructed of a non-porous material sized and dimensioned to receive at least a nipple portion of a breast of said patient and form a suction seal therewith;
    a solid phase sample collection medium in fluid connection with said breast engaging member for receiving a sample of expressed breast fluid;
    reciprocating means for reciprocally adjusting a position of said solid phase sample collection medium relative to said breast engaging member; and
    vacuum pump means in gaseous connection with said breast engaging member for generating negative pressure through said breast engaging member to facilitate breast fluid expression.

12. The sample collection device of claim 11, wherein said reciprocating means incorporates a support member or carrier reciprocatingly mounted relative to said breast engaging member, said support member or carrier supporting the solid phase sample collection medium.

13. The sample collection device of claim 11, wherein said solid phase sample collection medium is supported by a support member removably mounted in fluid connection with said breast engaging member.

14. The sample collection device of claim 13, wherein said support member is removably mounted to a carrier reciprocatingly mounted within a sample collection housing fluidly connected with said breast engaging member.

15. The sample collection device of claim 11, wherein said reciprocating means include a rotating member of a sample collection housing sealably and rotatably interconnected with said breast engaging member, said rotating member having a lumenal, helically oriented groove dimensioned to receive a riding peg extending transversely from a support member or carrier supporting said solid phase sample collection medium and a longitudinally oriented, lumenal groove dimensioned to receive an angularly fixating keel extending transversely from said carrier or support member, whereby rotation of the rotating member of the housing drives rotation of the carrier or support member and translates the riding peg along the helical groove to cause the support member or carrier to reciprocate forward or backward relative to the breast engaging member.

16. The sample collection device of claim 15, wherein said rotating member of said housing is removably interconnected with said breast engaging member to facilitate insertion and removal of said solid phase sample collection medium.

17. The sample collection device of claim 11, wherein said reciprocating means include a slide mechanism.

18. The sample collection device of claim 17, wherein said slide mechanism includes a manifold defining an inner lumen closed at one end to prevent gaseous connection with an outer lumen of a sample collection housing through which vacuum pressure is transmitted from said pump means to said breast engaging portion, and a sliding support member or carrier supporting said solid phase sample collection medium slideably mounted within said inner lumen.

* * * * *